US012594243B2

(12) United States Patent
Wang et al.

(10) Patent No.: US 12,594,243 B2
(45) Date of Patent: Apr. 7, 2026

(54) PHARMACEUTICAL FORMULATIONS

(71) Applicant: THERACOSBIO, LLC, Marlborough, MA (US)

(72) Inventors: Feng Wang, Shanghai (CN); Ankit Shrivastava, Madhya Pradesh (IN); Rina Shah, Gujarat (IN); Brian Seed, Boston, MA (US); Vinay Patil, Maharashtra (IN); Michael J. Hadd, San Jose, CA (US); Fuxia Dong, Shanghai (CN); Vipan Dhall, Brampton (CA); Chunfeng Dai, Shanghai (CN); Joseph Ho-Lun Chau, Whistler (CA); Qiuhua Cai, Shanghai (CN)

(73) Assignee: THERACOSBIO, LLC, Marlborough, MA (US)

( * ) Notice: Subject to any disclaimer, the term of this patent is extended or adjusted under 35 U.S.C. 154(b) by 0 days.

(21) Appl. No.: 18/501,714

(22) Filed: Nov. 3, 2023

(65) Prior Publication Data

US 2024/0139109 A1 May 2, 2024

Related U.S. Application Data

(63) Continuation of application No. 17/494,455, filed on Oct. 5, 2021, now abandoned.

(30) Foreign Application Priority Data

Oct. 5, 2020 (WO) ................ PCT/CN2020/119816

(51) Int. Cl.
*A61K 9/20* (2006.01)
*A61K 9/00* (2006.01)
*A61K 9/28* (2006.01)
*A61K 31/70* (2006.01)

(52) U.S. Cl.
CPC ............ *A61K 9/2013* (2013.01); *A61K 9/006* (2013.01); *A61K 9/2054* (2013.01); *A61K 9/284* (2013.01); *A61K 31/70* (2013.01)

(58) Field of Classification Search
CPC .... A61K 9/2013; A61K 9/006; A61K 9/2054; A61K 9/284; A61K 31/70
See application file for complete search history.

(56) References Cited

U.S. PATENT DOCUMENTS

| | | | |
|---|---|---|---|
| 7,838,499 | B2 | 11/2010 | Chen et al. |
| 8,106,021 | B2 | 1/2012 | Chen et al. |
| 8,283,454 | B2 | 10/2012 | Liou et al. |
| 8,575,321 | B2 | 11/2013 | Chen et al. |
| 8,802,637 | B2 | 8/2014 | Chen et al. |
| 8,987,323 | B2 | 3/2015 | Cai et al. |
| 9,006,403 | B2 | 4/2015 | Liou et al. |
| 9,061,060 | B2 | 6/2015 | Seed et al. |
| 9,193,751 | B2 | 11/2015 | Xu et al. |
| 9,464,043 | B2 | 10/2016 | Roberge et al. |
| 9,725,478 | B2 | 8/2017 | Xu et al. |
| 9,834,573 | B2 | 12/2017 | Cai et al. |
| 10,093,616 | B2 | 10/2018 | Roberge et al. |
| 10,533,032 | B2 | 1/2020 | Cai et al. |
| 10,981,942 | B2 | 4/2021 | Cai et al. |
| 2006/0204570 | A1 | 9/2006 | Lee |
| 2012/0041069 | A1* | 2/2012 | Sesha ................. A61K 31/7034 514/635 |
| 2018/0116911 | A1 | 5/2018 | Li |
| 2020/0000728 | A1 | 1/2020 | Pedersen et al. |
| 2020/0289457 | A1 | 9/2020 | Hadd et al. |
| 2023/0372374 | A1 | 11/2023 | Hadd et al. |

FOREIGN PATENT DOCUMENTS

| | | | | |
|---|---|---|---|---|
| CN | 108239055 A | 7/2018 | | |
| WO | WO-2010/022313 A2 | 2/2010 | | |
| WO | WO-2011/153953 A1 | 12/2011 | | |
| WO | WO-2011153712 A1 | 12/2011 | | |
| WO | 2012072256 | 6/2012 | | |
| WO | WO-2019209998 A1 | 10/2019 | | |
| WO | 2019221684 | 11/2019 | | |
| WO | WO-2020186142 A1 | 9/2020 | | |
| WO | WO-2020219645 A1 | 10/2020 | | |
| WO | WO-2021092341 A1 | 5/2021 | | |
| WO | WO-2021176096 A1 * | 9/2021 | ........... | A61K 31/155 |
| WO | WO-2022076328 A1 | 4/2022 | | |
| WO | WO-2023225492 A1 | 11/2023 | | |

OTHER PUBLICATIONS

Aburahma et al., Novel sustained-release fast-disintegrating multi-unit compressed tablets of Iornoxicam containing Eudragit RS coated chitosan-alginate beads, Pharmaceutical Development and Technology, 2011, vol. 16, No. 4, pp. 316-330.

Allegretti et al., Safety and Effectiveness of Bexagliflozin in Patients with Type 2 Diabetes Mellitus and Stage 3a/3b CKD, Am J Kidney dis., May 14, 2019, vol. 74, No. 3, pp. 328-337.

Dhawan et al., Applications of Poly(ethylene oxide) in Drug Delivery System Part II, Pharmaceutical Technology, Sep. 2005, pp. 82-96.

Doelker et al., Morphological, Packing, flow and Tableting Properties of New Avicel types, Drug Dev Ind Pharmacy, 1995, vol. 21, pp. 643-661.

(Continued)

*Primary Examiner* — Robert A Wax
*Assistant Examiner* — Olga V. Tcherkasskaya
(74) *Attorney, Agent, or Firm* — Mintz, Levin, Cohn, Ferris, Glovsky and Popeo, P.C.

(57) ABSTRACT

The pharmacokinetic profile of the SGLT2 inhibitor bexagliflozin can be improved by formulating it as an extended release tablet. Compared with standard immediate-release dosage forms these tablets can permit a lower peak plasma concentration, $C_{max}$, while maintaining plasma concentrations at therapeutic levels for a desired period. This can be used, for instance, to administer lower doses while still providing the same pharmacological effect.

7 Claims, 2 Drawing Sheets

(56) References Cited

OTHER PUBLICATIONS

Halvorsen et al., A 24-week, randomized, double-blind, active-controlled clinical trial comparing bexagliflozin with sitaliptin as an adjunct to metformin for the treatment of type 2 diabetes in adults, Diabetes Obes Metab, 2019, vol. 21, pp. 2248-2256.

Havorsen et al., a 96 week, multinational, randomized, double-blind, parallel-group, clinical trial evaluating the safety and effectiveness of bexagliflozin as a monotherapy for adults with type 2 diabetes, Diabetes Obes Metab., 2019, pp. 1-9.

Hou et al., Gastric Retentive Dosage Forms: A Review, Critical Review™ in Therapeutic Drug Carrier Systems, 2003, vol. 20, No. 6, pp. 461-497.

International Search Report for International Application No. PCT/CN2020/119816 mailed Jul. 1, 2021, 5 pages.

International Search Report for International Application No. PCTUS2021053416, mailed Jan. 16, 2022, 4 pages.

Opota et al., The Efficiency Of Glyceryl Behenate As Sustained-Release Agent Compared With Hydroxypropylcellulose In Tablets, International Journal of PharmTech, 2013, vol. 5, pp. 622-628.

Ray et al., Designing and In-Vitro Studies of Gastric floating Tablets of Tramadol Hydrochloride, 2010, International Journal of Applied Pharmaceutics, 2010, vol. 2, No. 4, pp. 12-16.

Srikanth Meka et al., Preparation and in vitro characterization of non-effervescent floating drug delivery system of poorly soluble drug, carvedilol phosphate, Acta Pharm., 2014, vol. 64, pp. 485-494.

Wei et al., Design and Evaluation of a Two-Layer Floating Tablet for Gastric Retention Using Cisaride as a Model Drug, Drug Development and Industrial Pharmacy, 2001, vol. 27, No. 5, pp. 469-474.

Written Opinion for International Application No. PCT/CN2020/119816, mailed Jul. 1, 2021, 7 pages.

Written Opinion for International Application No. PCTSU2021053416, mailed Jan. 19, 2022, 6 pages.

Zhang et al., EGT1442, a potent and selective SGLT2 inhibitor, attenuates blood glucose and $HbA_{1c}$ levels in db/db mice and prolongs the survival of stroke-prone rats, Pharmacological Research, 2011, vol. 63, No. 4, pp. 284-293.

Zhang et al., Metabolism and disposition of the SGLT2 inhibitor bexagliflozin in rats, monkeys and humans, Xenobiotica, 2019, pp. 1-11.

Exhibit D, <711> Dissolution, Stage 6 Harmonization, The United States Pharmacopeial Convention, Dec. 1, 2011, p. 1-8.

Sako, Journal of Pharmaceutical Science and Technology, Japan, 2004, 64(3):153-158 (partial English translation).

* cited by examiner

PHARMACEUTICAL FORMULATIONS

CROSS-REFERENCES TO RELATED APPLICATIONS

This application is a continuation of U.S. patent application Ser. No. 17/494,455 filed Oct. 5, 2021, which claims priority to International Application No. PCT/CN2020/119816, filed on Oct. 5, 2020, the entirety of which is incorporated herein by reference for all purposes.

TECHNICAL FIELD

The invention provides pharmaceutical formulations of SGLT2 inhibitors useful for treating diabetes mellitus and other conditions, and in particular oral formulations of bexagliflozin with improved pharmacokinetic properties.

BACKGROUND OF THE INVENTION

Bexagliflozin (EGT0001442, EGT1442, THR1442, THR0001442) is an inhibitor of SGLT2 (renal $Na^+$/glucose transporter) that is useful for the treatment and management of various conditions, including diabetes (see: Zhang et al. (2011) *Pharmacol Res* 63(4):284-93; Allegretti et al. (2019) *Am J Kidney Dis.* 74:328 doi: 10.1053/j.ajkd.2019.03.417; Zhang et al. (2019) *Xenobiotica* doi: 10.1080/00498254.2019.1654634). It has been tested in humans in the form of oral solid dosage forms (e.g. see NCT01377844 or NCT01029704) as well as oral solutions, and has been shown to be well-tolerated and to provide a durable, clinically meaningful improvement in glycemic control, as well as a reduction in body mass and blood pressure in diabetic adults (Halvorsen et al. (2019) *Diabetes Obes Metab* doi: 10.1111/dom.13833, Halvorsen et al. (2019) *Diabetes Obes Metab* 21:2248 doi: 10.1111/dom.13801).

SUMMARY OF THE INVENTION

Studies of human subjects who have been administered bexagliflozin in the form of oral capsules or oral solutions have shown that the plasma concentration of bexagliflozin displays a high peak/trough ratio (both $C_{max}$ to $C_{min}$ and $C_{max}$ to $C_{24h}$), with a steep decline during the alpha phase. The inventors have found that a better pharmacokinetic profile can be achieved by formulating bexagliflozin as an extended release tablet. Compared with standard immediate-release dosage forms, these tablets can permit lower doses to be administered while still providing the same pharmacological effect (a lower peak plasma concentration, $C_{max}$, while maintaining plasma concentrations at therapeutic levels), and can reduce the likelihood of side effects for any given dose. It is well known in the art that adverse drug reactions, especially poorly predictable idiosyncratic reactions (which frequently are not detected during the pre-approval testing of new drugs but, once discovered, can lead to restriction or withdrawal of the approved medication) are more likely to occur in drugs that must be administered in large doses, and that the likelihood of adverse reactions often increases as the $C_{max}$ increases. Thus, in a first aspect, the invention provides an extended release tablet of bexagliflozin.

A particularly preferred tablet of the first aspect releases bexagliflozin in vivo to provide a plasma $C_{max}$ in fasted subjects which is at least 125,000× lower per milliliter than the tablet's total bexagliflozin content. Thus, for example, a tablet containing 20 mg bexagliflozin would provide a fasted $C_{max}$ of ≤160 ng/mL. Ideally the plasma $C_{max}$ is at least 135,000× lower than the bexagliflozin content (i.e. ≤148 ng/mL for a tablet containing 20 mg bexagliflozin), or even at least 145,000× lower (i.e. ≤138 ng/mL for a 20 mg tablet).

According to a second aspect, the invention provides an extended release tablet that contains between 10 mg and 20 mg of bexagliflozin and that provides an in vivo plasma $C_{max}$ of ≤160 ng/mL in fasted subjects. Ideally the $C_{max}$ is ≤133 ng/mL. In one embodiment, the tablet contains 10 mg bexagliflozin and the $C_{max}$ is ≤80 ng/mL; in another embodiment, the tablet contains 20 mg bexagliflozin and the $C_{max}$ is ≤160 ng/mL.

According to a third aspect, the invention provides an extended release tablet that contains between 30 mg and 60 mg of bexagliflozin and that provides an in vivo plasma $C_{max}$ of <400 ng/mL in fasted subjects. In one embodiment, the tablet contains 40 mg bexagliflozin and the plasma $C_{max}$ is <320 ng/mL; in another embodiment, the tablet contains 50 mg bexagliflozin and the plasma $C_{max}$ is <400 ng/mL.

For both the first and second aspects, a preferred tablet contains 20 mg bexagliflozin and provides an $AUC_{0-t}$ between 600 and 1200 ng h $mL^{-1}$ in fasted subjects. Similarly, a preferred tablet contains 20 mg bexagliflozin and provides an $AUC_{0-\infty}$ *between* 675 and 1275 ng h $mL^{-1}$ in fasted subjects.

For both the first and second aspects, a preferred tablet contains 20 mg bexagliflozin and provides a plasma $C_{max}$ between 80 and 150 ng/mL in fasted subjects.

For the first, second and third aspects, a preferred tablet provides a bexagliflozin plasma concentration 24 hours after administration (i.e. $C_{24h}$) of ≥5 ng/mL, and ideally ≥10 ng/mL.

For the first, second and third aspects, a preferred tablet provides a time to maximum bexagliflozin plasma concentration (i.e. $T_{max}$) that is between 2 and 6 hours in fasted subjects, and ideally between 2 and 4.5 hours.

As explained in more detail below, the properties defined for a tablet will typically be measured after administration of representative specimens of a batch of which that tablet is an exemplar, and an appropriate average (e.g. geometric mean) of the results will be calculated. With this in mind, a batch of tablets according to the first aspect may release bexagliflozin in vivo to provide a geometric mean plasma $C_{max}$ in fasted subjects which is at least 125,000× lower per milliliter than each tablet's total bexagliflozin content. Similarly, a batch of tablets according to the second aspect may provide, an in vivo geometric mean plasma $C_{max}$ of ≤160 ng/mL (e.g. a geometric mean $C_{max}$ ≤133 ng/mL) in fasted subjects; for instance, tablets may contain 10 mg bexagliflozin and provide a geometric mean $C_{max}$ ≤80 ng/mL, or they may contain 20 mg bexagliflozin and provide a geometric mean $C_{max}$ ≤160 ng/mL. Similarly, a batch of tablets according to the third aspect may provide an in vivo geometric mean plasma $C_{max}$ of <400 ng/mL in fasted subjects; for instance, tablets may contain 40 mg bexagliflozin and provide a geometric mean plasma $C_{max}$ <320 ng/mL, or may contain 50 mg bexagliflozin and provide a geometric mean plasma $C_{max}$ <400 ng/mL. Furthermore, a batch of tablets of the first and second aspects containing 20 mg bexagliflozin may provide in fasted subjects (i) a geometric mean $AUC_{0-t}$ between 600 and 1200 ng h $mL^{-1}$ and/or (ii) a geometric mean $AUC_{0-\infty}$ between 675 and 1275 ng h $mL^{-1}$ and/or (iii) a geometric mean plasma $C_{max}$ between 80 and 150 ng/mL. Similarly, for the first, second and third aspects, a batch of tablets may provide a geometric mean $C_{24h}$ of ≥5 ng/mL, and ideally ≥10 ng/mL.

For a batch of tablets according to the first, second and third aspects, the ratio of the median bexagliflozin plasma $C_{max}$ and $C_{min}$ values may be less than 10 e.g. between 5-10, between 6-8, or between 7-8. The high peak/trough ratio seen in the prior art can thus be avoided. A median $C_{min}$ of at least 10 ng/mL is preferred. As shown below, these pharmacokinetic parameters represent robust statistical estimates based on measurements from over 800 subjects from various regions in the world, using various different extended release bexagliflozin tablets.

The inventors have also observed that bexagliflozin is a P-gp substrate, and that absorption of bexagliflozin from the large intestine is minimal. Because P-gp expression increases with distance along the small intestine, absorption is likely greater in the duodenum than the ileum, and quantitative mass balance studies using [$^{14}$C]-bexagliflozin have shown that colonic absorption is minimal (Zhang et al. *Xenobiotica*. 2019 Aug. 27:1-11. doi: 10.1080/00498254.2019.1654634). Because of the potential practical incompatibility of using an extended release tablet while aiming for most drug release to occur high in the small intestine, tablets of the invention advantageously include an adaptation that can help to retain them in the stomach. A large part of the extended release of bexagliflozin can thus occur in the stomach, permitting absorption of the drug to occur at the desired location in the small intestine, thereby providing an advantageous pharmacokinetic profile. Tablets with gastric retention adaptations have been shown to function well in vivo even though bexagliflozin is unstable in the prolonged presence of acid, and is susceptible to acidic decomposition.

Various adaptations can be used to help retain a tablet of the invention in the stomach, including but not limited to: (i) inclusion of an effervescent excipient, which can provide buoyancy during gaseous release in stomach acid; (ii) rapid gastric dispersal into multiple granules or pellets, thereby avoiding expulsion of the complete tablet from the stomach in a single event; (iii) the use of low density excipients to provide a buoyant or floating tablet; and/or (iv) the inclusion of a mucoadhesive in the tablet. These four approaches can be used individually or together to provide advantageous tablets for delivery of bexagliflozin.

According to a fourth aspect, the invention provides an extended release tablet that contains bexagliflozin and a mucoadhesive. Ideally, this tablet has a density below that of gastric contents. It can also be effervescent (particularly when in contact with gastric acid) and/or it can disperse into multiple granules or pellets when it comes into contact with gastric acid.

According to a fifth aspect, the invention provides a solid oral dosage form, typically an extended release tablet, that contains bexagliflozin and that in an in vitro dissolution test in simulated gastric fluid (see below) releases ≤17% of its bexagliflozin after 1 hour and releases ≥80% after 8 hours. In one embodiment, it releases between 20-45% (inclusive) of its bexagliflozin after 3 hours, and/or between 45-75% (inclusive) of its bexagliflozin after 5 hours. This tablet can be from a manufacturing batch of tablets which pass the formal dissolution acceptance criteria discussed below.

According to a sixth aspect, the invention provides a solid oral dosage form, typically an extended release tablet, that contains bexagliflozin and that in an in vitro dissolution test in simulated gastric fluid (see below) has a $f_2$ value of >50 when compared to a reference tablet, wherein $f_2$ is proportional to the decimal logarithm of one plus the mean squared error:

$$f_2 = 100 - 25\ \log_{10}\left(1 + n^{-1}\sum_{i=1}^{n}(R_i - T_i)^2\right)$$

where: n is number of time points at which dissolution is measured; $R_i$ is the dissolution percentage of a reference tablet at the i-th timepoint; and $T_i$ is the dissolution percentage of the solid oral dosage form at the i-th timepoint;

and where the reference tablet is an extended release tablet that contains bexagliflozin and that, in an in vitro dissolution test in simulated gastric fluid, releases ≤17% of its bexagliflozin at 1 hour, releases ≥80% at 8 hours and, optionally, releases between 20-45% (inclusive) of its bexagliflozin at 3 hours and/or 45-75% (inclusive) of its bexagliflozin at 5 hours. Three suitable reference tablets are disclosed in more detail below as reference tablets (a) to (c), where tablet (c) is preferred. The value of n is preferably at least 3 e.g. between 4-8.

According to a seventh aspect, the invention provides a batch of extended release bexagliflozin tablets wherein, upon administration to a cohort of healthy fasted subjects, a first representative sample set of tablets from the batch provides on one occasion a first mean logarithm of $C_{max}$ and a first mean logarithm of $AUC_{0-t}$, and a second representative sample of tablets from the batch produces on a different occasion a second mean logarithm of $C_{max}$ and a second mean logarithm of $AUC_{0-t}$, and wherein the differences between the first and second mean logarithms of $C_{max}$ and between the first and second mean logarithms of $AUC_{0-t}$ both exhibit 90% confidence intervals having endpoints which lie between −0.22314 and +0.22314. Details on assessing these parameters are given in the section 'Bioequivalence' below e.g. the use of a random crossover study in a suitable test population, etc. Ideally each tablet in the batch contains 5 mg, 10 mg, or 20 mg of bexagliflozin.

According to an eighth aspect, the invention provides a batch of extended release bexagliflozin tablets wherein, upon administration to a cohort of healthy subjects each provided on one occasion a single tablet from a first representative tablet sample set in the fasted state, and on a different occasion a single tablet from a second representative tablet sample set in the fed state (e.g., 30 minutes following a standard high fat, high calorie meal, as described in the section 'Bioequivalence' below and references therein), the mean differences in $\ln(C_{max})$ and $\ln(AUC_{0-t})$ (created by subtracting the values for the logarithms of $C_{max}$ and the logarithms of $AUC_{0-t}$ for the fasted state from the values for the logarithms of $C_{max}$ and the logarithms of $AUC_{0-t}$ for the fed state) both exhibit a 90% confidence interval with endpoints which lie between −0.22314 and +0.58779. Ideally each tablet in the batch contains 5 mg, 10 mg, or 20 mg of bexagliflozin.

According to a ninth aspect, the invention provides a batch of extended release bexagliflozin tablets wherein, upon administration to a cohort of fasted healthy subjects each provided on one occasion a single tablet from a first representative tablet sample set without any prior dosage of a parenteral GLP-1 receptor agonist, and on a different occasion a single tablet from a second representative tablet sample set 30 minutes following an approved dosage of a parenteral GLP-1 receptor agonist, the mean differences in $\ln(C_{max})$ and $\ln(AUC_{0-t})$ (created by subtracting the values of the logarithms of $C_{max}$ and the logarithms of $AUC_{0-t}$ for the first sample set from the values of the logarithms for the second sample set) both exhibit a 90% confidence interval with an upper bound of less than 0.69315. Ideally each tablet in the batch contains 5 mg, 10 mg, or 20 mg of bexagliflozin.

According to a tenth aspect, the invention provides a batch of extended release bexagliflozin tablets wherein, upon administration to a cohort of healthy subjects each provided on one occasion a single tablet from a first representative tablet sample set in the fasted state, and on a different occasion, a single tablet from a second representative tablet sample set in the fed state (e.g., 30 minutes following a standard high fat, high calorie meal as described in the section 'Bioequivalence' below), the differences created by subtracting the values for the $T_{max}$ for the fasted state from the values for the $T_{max}$ for the fed state exhibit a median that is less than or equal to 3.5 hours. The median difference is the difference for which 50% of the subjects have values above the median and 50% of subjects have values below the median; for example in an ordered listing of the differences, for an odd number of subjects (e.g., 2n+1 subjects), the median is the difference for the subject in the list midpoint, (subject n+1), and for an even number of subjects (e.g., 2n subjects), the median is the arithmetic average of the differences for the two subjects flanking the midpoint (subjects n and n+1). Ideally each tablet in the batch contains 5 mg, 10 mg, or 20 mg of bexagliflozin.

According to an eleventh aspect, the invention provides a solid oral dosage form, typically an extended release tablet, that contains bexagliflozin and that provides a first plasma $C_{max}$, a first $AUC_{0-t}$ and a first $T_{max}$ in fasted subjects, and provides a second plasma $C_{max}$, a second $AUC_{0-t}$ and a second $T_{max}$ in fed subjects, wherein (i) the ratio of the second divided by the first $C_{max}$ is between 0.8 and 1.8; (ii) the ratio of second divided by the first $AUC_{0-t}$ is between 0.8 and 1.8; or (iii) the ratio of second divided by the first $T_{max}$ is between 0.8 and 3.0.

As explained below, the properties defined for such a tablet will typically be measured after administration of representative specimens of a batch of which that tablet is an exemplar. Thus a batch of tablets of the eleventh aspect can provide a first geometric mean plasma $C_{max}$, a first geometric mean $AUC_{0-t}$ and a first median $T_{max}$ in fasted subjects, and provides a second geometric mean plasma $C_{max}$, a second geometric mean $AUC_{0-t}$ and a second median $T_m$ in fed subjects, wherein (i) the ratio of the second divided by the first geometric mean $C_{ma}$ is between 0.8 and 1.8; (ii) the ratio of second divided by the first geometric mean $AUC_{0-t}$ is between 0.8 and 1.8; or (iii) the ratio of second divided by the first median $T_{max}$ is between 0.8 and 3.0.

According to a twelfth aspect, the invention provides a solid oral dosage form, typically an extended release tablet, that contains bexagliflozin and that provides a first plasma $C_{max}$, a first $AUC_{0-t}$ and a first $T_{max}$ in subjects not previously administered a parenteral GLP-1 receptor agonist, and provides a second plasma $C_{max}$, a second $AUC_{0-t}$ and a second $T_{max}$ in subjects previously administered a parenteral GLP-1 receptor agonist, wherein (i) the ratio of the second divided by the first $C_{max}$ is between 0.8 and 2.0; (ii) the ratio of second divided by the first $AUC_{0-t}$ is between 0.8 and 2.0; or (iii) the ratio of second divided by the first $T_{max}$ is between 0.8 and 3.0.

As explained below, the properties defined for such a tablet will typically be measured after administration of representative specimens of a batch of which that tablet is an exemplar. Thus a batch of tablets of the twelfth aspect can provide a first geometric mean plasma $C_{max}$, a first geometric mean $AUC_{0-t}$ and a first median $T_{max}$ in subjects not previously administered a parenteral GLP-1 receptor agonist, and provides a second geometric mean plasma $C_m$, a second geometric mean $AUC_{0-t}$ and a second median $T_{max}$ in subjects previously administered a parenteral GLP-1 receptor agonist, wherein (i) the ratio of the second divided by the first geometric mean $C_{max}$ is between 0.8 and 2.0; (ii) the ratio of second divided by the first geometric mean $AUC_{0-t}$ is between 0.8 and 2.0; or (iii) the ratio of second divided by the first median $T_{max}$ is between 0.8 and 3.0.

The invention also provides methods for treating patients as discussed in more detail below.

BRIEF DESCRIPTION OF DRAWINGS

(FIG. 3A) or 30° C. (FIG. 3B). The graph shows measured means with a line of regression.

DETAILED DESCRIPTION OF THE INVENTION

Figure 1:
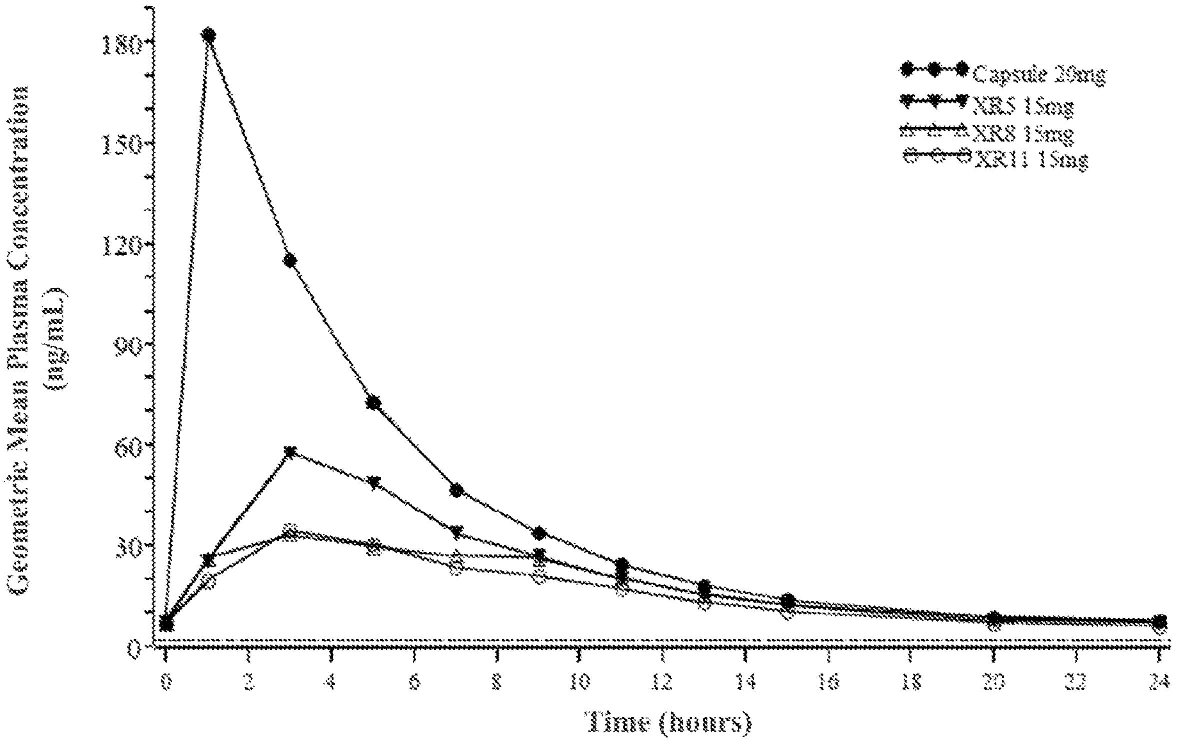
FIG. 1 shows the geometric mean plasma concentration (ng/mL) of bexagliflozin in fasted subjects as a function of time post-dose (hours). Closed circles (●) show data for 20 mg capsules, whereas the other symbols are for 15 mg tablets XR5 (▼), XR8 (A), or XR11 (○).

The invention provides extended release tablet formulations that provide improved pharmacokinetic properties for bexagliflozin when compared to capsule formulations.

Bexagliflozin

Bexagliflozin is a SGLT2 inhibitor in the C-aryl glucoside class and has formula (I):

(I)

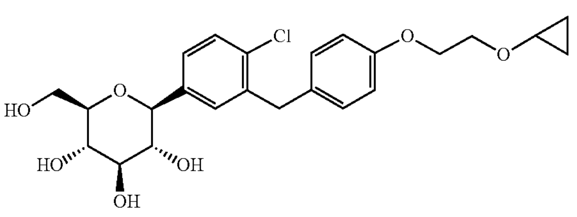

Its IUPAC name is (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol. Its CAS registry number is 1118567-05-7.

Tablets of the invention include bexagliflozin, usually in the form of a crystalline solid (e.g. see WO2011/153953). In some embodiments bexagliflozin may be present in the form of an ester (mono-, di-, tri-, or tetra-) but usually bexagliflozin will be used as the tetraol of formula (I) as shown above. Furthermore, in some embodiments bexagliflozin may be present in the form of a co-crystal e.g. a co-crystal with proline, such as 'THR1474' (bexagliflozin:proline at a 1:2 molar ratio) as disclosed in WO2010/022313. These forms of bexagliflozin may optionally be present in tablets of the invention as a solvate. The invention encompasses all such forms of bexagliflozin.

The amount of bexagliflozin in a tablet of the invention will generally range from 1 mg to 100 mg, and is preferably within the range of 5 mg to 50 mg (e.g. 10-20 mg for the second aspect of the invention). Tablets containing 5 mg, 10 mg, or 20 mg are particularly preferred. These values are expressed in terms of the tetraol of formula (I). Extended release tablets of these strengths (and in particular 20 mg) offer good therapeutic effects.

References to a particular content of bexagliflozin in a tablet will be understood in the normal context of pharmaceutical formulation. Thus, content may be measured, for instance, in line with USP General Chapter <905>, Ph. Eur. 2.9.40 Uniformity of Dosage Units, or JP 6.02 Uniformity of Dosage Units. Where a tablet is licensed for medicinal use in a particular territory then the relevant licence, marketing authorization, prescribing information, summary of product characteristics, product information, patient literature, etc., will specifically mention the amount of bexagliflozin therein e.g. a tablet dosage form with a strength of 5 mg, 10 mg, 20 mg, 40 mg, or 50 mg.

It is possible that tablets of the invention may include bexagliflozin-related impurities and/or degradation products. If so, these should be present at ≤1.0% of the total mass of bexagliflozin in the tablet, and any particular impurity or degradation product should be present at ≤0.20% of the total mass of bexagliflozin.

General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted when defining the invention.

The term "between" with reference to two values includes those two values e.g. the range "between" 10 mg and 20 mg encompasses inter alia 10, 15, and 20 mg.

The inferred pharmacokinetic parameters of a noncompartmental analysis are here defined as most frequently employed in the art and summarized in the following:

"$T_{max}$" is the time at which the greatest observed plasma concentration is recorded and, when presented for a population, is, unless otherwise described, given as the population median.

"$C_{max}$" is the greatest observed plasma concentration.

"$C_{min}$" is the lowest observed plasma concentration, typically obtained as the value prior to a repeat dosing in a regularly scheduled dosing regimen. For example, for daily dosing $C_{min}$ is often recorded 24 hours after the previous dose.

"AUC" is the "area under the curve" of the plasma concentration as a function of time, constructed by the linear trapezoidal rule, according to which the AUC is given by the summation of the arithmetic mean of the concentration at two adjacent sampling points in time, multiplied by the difference in time between those sampling points: $(C(t_i)+C(t_{i+1}))(t_{i+1}-t_i)/2$.

"$AUC_{0-t}$" represents the AUC from time 0 (e.g. the time of ingestion) to the last quantifiable concentration.

"$AUC_{0-\infty}$" represents the AUC from time 0 to infinity, as produced by extrapolation of a simple (monophasic) exponential decay. $AUC_{0-\infty}=AUC_{0-t}+C_{last}/k_{el}$, where $C_{last}$ is the last quantifiable concentration and $k_{cl}$ is the terminal elimination rate constant.

"$t_{1/2}$" is the terminal half-life, also referred to as the elimination half-life. If the empirically determined terminal elimination kinetics are not first-order in time, $t_{1/2}$ cannot be defined. $T_{1/2}=-\ln(2)/k_{el}\approx 0.693/k_{el}$.

The terms "d(0.1)", "d(0.5)" and "d(0.9)" describe the threshold diameters for particles falling in the smallest 10%, 50% and 90% of the total volume of all particles. Thus at d(0.9), 90% of the volume of the sample can be found in particles of smaller diameter than d(0.9).

The "logarithm" as used herein refers by default to the natural logarithm, often written as a function of argument x as ln(x), where for avoidance of doubt, $x=e^{ln(x)}$. If the base of the logarithm is 10, the logarithm is referred to as the decimal logarithm, and written as a function of argument y as $\log_{10}(y)$, where, for avoidance of doubt, $y=10^{log_{10}(y)}$.

A "solid oral dosage form" herein can be any solid (or semi-solid) dosage form which can be administered orally. It can take the form of a tablet, a solid pill, a capsule, a caplet, an encapsulated gel or encapsulated liquid, or combinations or concretions of such as may be present in layers or subcomponents such as beads, droplets or particles of various shapes and of differing properties embedded in a matrix or contained in a capsule or caplet.

A "batch" of tablets can range in size from 100 tablets up to a complete manufacturing batch (e.g. all of the tablets that are made from the same initial quantity of material and have undergone the same series of manufacturing operations, or any aggregate quantity of tablets that have undergone similar manufacturing operations and are pooled for testing or distribution purposes). The definition of "manufacturing batch" includes that provided by 21 USC 201.3 i.e. a "specific quantity of a drug or other material that is intended to have uniform character and quality, within specified limits, and is produced according to a single manufacturing order during the same cycle of manufacture."

The word "representative", when applied to a unit or sample of a batch, means a unit or sample that is not pre-selected for any particular character, such as weight, density, hardness or hue of coating, that is free from manufacturing defects and that is drawn substantially at random from the batch.

The phrase "substantially at random" means either completely at random, such that every unit in the batch has an equal probability of being selected, or chosen by a process that aims to achieve a practical balanced representation of the batch being sampled. For example, representative units may be drawn at regular intervals during production or coating to avoid a sampling imbalance in which units with slightly different properties, e.g. as produced from the beginning or end of a run, are overrepresented. Such units would be said to be drawn substantially at random from the batch.

A "sample set" as used herein refers to a collection of units or samples that can be individually or collectively analyzed to estimate the properties of a batch or population as a whole. When used in connection with in vitro or in vivo testing of tablet properties, the sample set refers to a collection that is individually tested, and from which the properties of the batch of tablets as a whole are estimated.

The properties defined for any particular unit (e.g. a tablet) are to be understood as being the properties of a representative unit drawn from a manufacturing batch, the members of which impart or exhibit the referenced properties in an appropriate test typically consuming multiple units from the manufacturing batch. Thus, when a unit is said to produce a particular pharmacokinetic parameter, it will be understood that this parameter will typically be measured after administration of representative specimens of a manufacturing batch of which that unit is an exemplar, and an appropriate statistical characterization of the results will be calculated. Parameters based on plasma bexagliflozin concentrations (e.g. $C_{max}$ and AUC) will typically be characterized as geometric means, whereas the $T_{max}$ will typically be characterized by the population median. Furthermore, when a pharmacokinetic parameter is defined as having a certain range of values, it is to be understood that administration of representative specimens of a manufacturing batch of which that unit is an exemplar would produce, in an appropriately constituted experimental cohort, the characterized parameter (e.g., the geometric mean or the median) falling within the stated range of values.

For instance, when tablets are said to produce a statistical measure (e.g., a geometric mean $C_{max}$) falling within a certain range of values, it is to be understood that administration of representative specimens of a manufacturing batch of which that tablet is an exemplar would produce, in an appropriately constituted cohort, the statistical measure (e.g., the geometric mean $C_{max}$) falling within the stated range of values.

An "appropriately constituted cohort" refers to a collection of test subjects that typically consists of healthy individuals of both sexes in a sample size that provides appropriate power to estimate the desired pharmacokinetic parameter. A sample size that provides appropriate power can be calculated as described below. In routine practice, for example to demonstrate bioequivalence for regulatory purposes, twelve or more subjects of each sex are often employed, or a total sample size of 24 subjects if sex is not balanced. It is typical to request that the participants in a test of this sort abstain from consumption of alcohol and avoid ingestion of foods known to substantially influence the metabolism of drugs. Although it is not, for example, a regulatory requirement, it is to be understood that for the purposes of determining whether or not a sample set represents tablets of the present invention, the experimental cohort should be constituted from individuals near the midpoint of the healthy population of young adults as a whole, so that for example the cohort would not contain a preponderance of individuals of high or low body mass, or exceptionally lean or obese habitus, or of elderly individuals or individuals with unusual dietary habits or consumptions of medications, herbal preparations or supplements that might confound the measurements.

A "sample size that provides appropriate power" to estimate a pharmacokinetic parameter is the number of individuals in the cohort needed to achieve a discrimination of a particular degree between groups subjected to two experimental conditions, for example, having consumed tablets from one source or tablets from another. Methods of calculating statistical power are well-known in the art. In its simplest form, statistical power describes the probability of obtaining a statistically significant result in a study when the predicted difference actually exists between two populations. A power calculation is often cast as the determination of the minimum sample size to detect a true intergroup difference with a specified likelihood of failure due to randomness. For example a 90% power means that in 9 out of ten studies a statistically significant result will emerge, but in 1 out of 10, significance will not be achieved even though the difference is present. Hence 100% minus the power is the probability of a false negative. Typical power values in testing pharmacokinetic parameters are 90% or greater and for definiteness "appropriate power" will be defined here as 95% or greater. To perform a power calculation, the variability in the measure to be taken, usually expressed as a standard deviation, and the difference to be detected (the difference in the values of the measure from the two groups to be detected) must be input. If there is substantial uncertainty about the standard deviation of a measure in a population, it can be empirically determined. When used in the setting of noninferiority determinations, power calculations are used to estimate the sample size needed to confirm that the difference between two groups is less than a certain quantity. For example bioequivalence studies are two-sided noninferiority tests that aim to demonstrate that the difference between two preparations falls within certain bounds.

When the prandial state, e.g., fasted or fed, is specified, the fasted state is to be achieved by each subject by refraining from consumption of food or beverages other than water for at least ten hours prior to ingestion of a tablet and the fed state is to be achieved by each subject by consumption of a standard high fat, high caloric content meal as provided by regulatory guidance (e.g., *FDA Guidance for Industry: Bioavailability and Bioequivalence Studies Submitted in NDAs or INDs—General Considerations*, March 2014), with ingestion of the tablet 30 minutes after consumption of the meal is initiated. Further information on how these specific prandial states are to be achieved is provided below in the section Bioequivalence.

Extended Release Tablets

Bexagliflozin has been administered to human subjects in several dosage forms. A 50 mg dose of bexagliflozin delivered as an aqueous solution to healthy male volunteers in a radiolabeled tracer mass balance study has been found to produce a $C_{max}$ of 692 ng $mL^{-1}$, an $AUC_{0-t}$ of 2523 ng h $mL^{-1}$ and an $AUC_{0-\infty}$ of 2604 ng h $mL^{-1}$; the $T_{max}$ was 0.5 h and the $t_{1/2}$ 5.6 h (Zhang et al. (2019), op. cit.). The dose-normalized $C_{max}$ was 13.84 ng $mL^{-1}$ per mg bexagliflozin.

Oral administration of a capsule formulation of bexagliflozin has been well tolerated by healthy and diabetic subjects at single and repeated doses of up to 100 mg. Capsules provide relatively rapid in vivo release of bexagliflozin, but subsequent plasma concentrations display a high peak/trough ratio. Capsules containing 6.7, 16.7 and 34 mg bexagliflozin have produced a dose-normalized $C_{max}$ following ingestion in the fasted state of 12.6, 11.3 and 11.5 ng $mL^{-1}$ $mg^{-1}$ bexagliflozin, respectively, with median $T_{max}$ values of 1, 2 and 1 h, respectively. Based on these values a capsule containing 20 mg of bexagliflozin, for instance, displays a $C_{max}$ of between 226 and 252 ng/mL in fasted subjects, occurring about 1 to 2 hours after administration (i.e. $T_{max}$ of about 1 to 2 hours). The rate of absorption is most rapid for an oral solution, which shows the smallest $T_{max}$ and the greatest dose-normalized $C_{max}$. Capsules containing 34 mg produced a $C_{24h}$ of greater than 10 ng/mL. The plasma concentration displays a steep decline during the alpha phase (i.e. the distribution phase of a standard two-compartment model).

Compared with an immediate release capsule, the inventors have found that the pharmacokinetic profile of bexagliflozin can be improved by formulating bexagliflozin as an extended release tablet. These tablets can provide a lower $C_{max}$ (e.g. 8 ng/mL per mg bexagliflozin or below) while still maintaining a $C_{24h}$ of about 10 ng/mL for a 20 mg tablet. The reduced $C_{max}$ reduces the risk of side effects, but the medicine remains efficacious because near-maximal urinary glucose excretion is seen in dosage forms which are able to provide a plasma concentration 24 hours after dosing (i.e. $C_{24h}$) of 10 ng/mL or more.

The first aspect of the invention therefore provides an extended release tablet of bexagliflozin.

An extended release (also referred to as prolonged or sustained release) tablet releases its contents in vivo over an extended period of time following ingestion. Ideally release should begin promptly after ingestion (e.g. as soon as the tablet enters the stomach), and should not be delayed. Thus, a tablet of the invention will in general not have an enteric coating, as this would give a delayed release profile.

Tablets of the invention should provide a unimodal plasma concentration of bexagliflozin as a function of time (in most subjects). Thus, after a single tablet is administered to a subject, the subsequent plasma concentration of bexagliflozin should show only one peak (e.g. see FIG. 1 and FIG. 2).

Tablets of the invention can display substantially zero-order release of bexagliflozin in vitro.

The plasma concentration of bexagliflozin can decrease in a biphasic manner after reaching $C_{max}$.

As mentioned above, a capsule containing 20 mg of bexagliflozin displays a plasma $C_{max}$ of about 226 to 252 ng/mL in fasted subjects i.e. the $C_{max}$ per milliliter of plasma is 80,000 to 90,000× lower than the capsule's total bexagliflozin content. In preferred tablets of the invention, however, $C_{max}$ in fasted subjects should be at least 125,000× lower than the tablet's bexagliflozin content. Thus, a 20 mg tablet would provide $C_{max}$≤160 ng/mL. Ideally, the ratio of $C_{max}$ to bexagliflozin content is even higher than 125,000×, for example ≥135,000× or ≥145,000×.

Thus, the invention in particular provides an extended release tablet which provides an in vivo geometric mean plasma $C_{max}$ of ≤8 ng/mL per mg of bexagliflozin in the tablet (ideally ≤6 ng/mL per mg bexagliflozin) in fasted healthy subjects (e.g. in a cohort of not less than 6 fasted subjects having a body mass greater than 60 kg). In one embodiment the tablet contains 10 mg bexagliflozin and provides a $C_{max}$ of ≤80 ng/mL; in another embodiment, the tablet contains 20 mg bexagliflozin and provides a $C_{max}$ of ≤160 ng/mL.

Where a tablet of the invention provides a $C_{max}$ of ≤160 ng/mL, this is preferably ≤150 ng/mL, and is ideally between 80-150 ng/mL (particularly for a 20 mg bexagliflozin dose). A preferred 20 mg tablet provides a $C_{max}$ between 85-145 ng/mL, and more preferably a $C_{max}$ between 95-140 ng/mL.

An extended release tablet of the invention should provide a bexagliflozin plasma $C_{24h}$ in fasted subjects of ≥3 ng/mL. As mentioned above, near-maximal urinary glucose excretion is seen with a plasma $C_{24h}$ of ≥10 ng/mL, so a preferred tablet of the invention can provide a plasma $C_{24h}$ of ≥10 ng/mL e.g. within the range of 10-25 ng/mL. In one embodiment the tablet contains 10 mg bexagliflozin and provides a $C_{24h}$ of ≥3 ng/mL; in another embodiment, the tablet contains 20 mg bexagliflozin and provides a $C_{24h}$ of ≥6 ng/mL.

As mentioned above, a capsule formulation of bexagliflozin displays a plasma $T_{max}$ of about 1 hour in a fasted subject. In contrast, preferred tablets of the invention can provide a $T_{max}$ in a fasted subject that is typically between 2 and 6 hours. Thus, tablets of the invention can delay bexagliflozin's $T_{max}$ when compared to immediate release capsules.

Preferred tablets of the invention provide a plasma $AUC_{0-t}$ between 15-60 ng h mL$^{-1}$ per mg of bexagliflozin in the tablet in a fasted subject. In one embodiment the tablet contains 10 mg bexagliflozin and provides $AUC_{0-t}$ of between 150-600 ng h mL$^{-1}$ e.g. between 350-450 ng h mL$^{-1}$; in another embodiment, the tablet contains 20 mg bexagliflozin and provides an $AUC_{0-t}$ of between 600-1200 ng h mL$^{-1}$ e.g. between 650-1150 ng h mL$^{-1}$.

Preferred tablets of the invention provide a plasma $AUC_{0-\infty}$ between 17.5-65 ng h mL$^{-1}$ per mg of bexagliflozin in the tablet in a fasted subject. In one embodiment the tablet contains 10 mg bexagliflozin and provides $AUC_{0-\infty}$ of between 410-510 ng h mL$^{-1}$; in another embodiment, the tablet contains 20 mg bexagliflozin and provides $AUC_{0-\infty}$ of between 675-1275 ng h mL$^{-1}$ e.g. between 750-1200 ng h mL$^{-1}$.

Preferred tablets of the invention provide a $t_{1/2}$ (terminal elimination half-life) in a fasted subject that is between 7 and 14 hours e.g. between 8 and 13 hours.

$C_{max}$, $T_{max}$, $t_{1/2}$, $C_{24h}$, $AUC_{0-t}$, and $AUC_{0-\infty}$ are standard pharmacokinetic parameters. They can be estimated manually or by using modelling software well known in the art, such as the Phoenix WinNonlin package using a non-compartmental model. The general basis for calculation of these quantities is well-known (e.g. see Rowland & Tozer (2019) *Clinical Pharmacokinetics and Pharmacodynamics: Concepts and Applications* ISBN 978-1496385048, or Jambhekar & Breen (2012) *Basic Pharmacokinetics* ISBN 978-0853699804). Typically, the parameters will be assessed as the average (e.g. geometric mean) from within a group of at least 12 (and normally between 24 and 36) healthy human adults. Parameters should be measured in accordance with standards and practices which would be acceptable to a pharmaceutical regulatory agency such as FDA, EMEA, MHLW, or WHO. The values may be based on measurements taken at appropriate intervals following the time of tablet ingestion, such as every hour, or at increasingly sparse sampling intervals, such as 1, 3, 5, 7, 9, 11, 13, 15, 20, and 24 hours after ingestion.

The pharmacokinetic parameters mentioned above were defined for the plasma of fasted human subjects i.e. subjects who have had a minimum of a 10-hour overnight fast. These parameters of bexagliflozin differ in fasted and fed subjects, and if the tablet is taken after eating (e.g. 30 minutes after starting a meal) then typically $C_{max}$, $C_{24h}$, $AUC_{0-t}$, and $AUC_{0-\infty}$ are all higher. The fasted subjects in whom the parameters as defined herein have been assessed, and should be measured, are fasted healthy (i.e. non-diabetic, and not medicated for other conditions) human adult Caucasian subjects (male and female) having a body mass between 60-100 kg e.g. a body mass about 75 kg. The same behavior may be seen in other subjects as well (e.g. in Asian subjects, or in patients with a lower body mass), but populations in whom the parameters are assessed should meet these criteria. Testing in a cohort of at least 6 subjects is typical.

Extended release tablets having the desired $C_{max}$, $T_{max}$, $C_{24h}$, $AUC_{0-t}$, and/or $AUC_{0-\infty}$ properties can be prepared by following the guidance given below, in conjunction with common general knowledge about the preparation of extended release tablets e.g. as described in Collett & Moreton (2007) chapter 32 of *Pharmaceutics: The Science of Dosage Form Design* (3$^{rd}$ edition), in Lordi (1986) chapter in *Theory and Practice of Industrial Pharmacy* (3$^{rd}$ edition), in Timmins et al. (2014) *Hydrophilic Matrix Tablets for Oral Controlled Release* ISBN 978-1493915187, in Sushma et al. (2014) *Matrix Tablets: An Approach Towards Sustained Release Drug Delivery* ISBN 978-3659579110, in Rasul et al. (2011) *Sustained Release Tablets* ISBN 978-3844323719, and in Eyjolfsson (2014) *Design and Manufacture of Pharmaceutical Tablets* ISBN 978-0128021828. Patel (2013) *Extended Release Tablet of Antidiabetic Drug: Development, Optimization and Evaluation*, ISBN 978-

3659448140, describes how an extended release tablet of glipizide was developed using hydroxyethyl- and hydroxypropyl-cellulose.

The principles of extended release tablet manufacture are thus well known in the art. Compared to an immediate release capsule of any particular dose, the use of extended release tablet technology reduces $C_{max}$ of bexagliflozin, in accordance with the desirable pharmacokinetic profile of the invention. The degree of the decrease can be controlled by modifying the characteristics of the extended release tablet, in line with known design principles.

There are three main ways in which extended release from a tablet is achieved: (i) by using a monolithic matrix, with drug particles dispersed in either a soluble matrix or an insoluble matrix; (ii) reservoir or membrane-controlled systems; or (iii) osmotic pump systems. A tablet based on a soluble matrix includes a compressed mixture of bexagliflozin and a water-swellable hydrophilic polymer, and on entering the GI tract the tablet starts to dissolve and release bexagliflozin over an extended period of time. A tablet based on an insoluble matrix includes a mixture of bexagliflozin and a wax or a water-insoluble substance, such as a fat or polymer, into which water can diffuse and dissolve the bexagliflozin to permit its release. The paths for water diffusion can be part of the tablet when it is swallowed, or they can emerge after ingestion as channeling agents leach from the tablet. A tablet based on a reservoir system includes a membrane through which bexagliflozin must diffuse, and hydration of the membrane permits this diffusion to occur. The membranes are generally made from polymers which remain intact during the period of release, such as acrylic copolymers, ethylcelluloses, shellac, and zein. The osmotic pump system is similar to the reservoir system, but hydration of the tablet core builds up a hydrostatic pressure which forces dissolved bexagliflozin through a hole in the core's semi-permeable coating. Details of suitable release-controlling agents for use in these tablets are given below.

These general approaches are well known and a person skilled in the art of tablet formulation will be able to make and test tablets utilizing any of these approaches and to adapt them according to the tablet's desired pharmacokinetic properties. A tablet's properties can be modified according to the characteristics of the formulation approach which is used. For instance: with a soluble matrix, the chemical nature, physical nature, and quantity of the water-swellable hydrophilic polymer can be chosen to control release; with a water-insoluble (such as a wax) matrix, the quantity of the water-insoluble substance and the nature and quantity of the channeling agent can be chosen to control release; with an insoluble polymeric matrix, the pore structure of the matrix is the key parameter, and a more rigid and less porous matrix will generally lead to slower release; with a reservoir system the choice of membrane is the key, and in particular the choice and quantity of membrane plasticizer, but addition of water-soluble components to the membrane can also be used to increase the rate of release; and with an osmotic pump system the rates at which water can enter the core, and at which bexagliflozin can leave the coating's hole, govern the tablet's release characteristics. The ingredients and design principles for controlling a tablet's release characteristics while providing a physically stable tablet are thus well known, and a person skilled in the art of tablet formulation can make and test (both in vitro and in vivo) tablets utilizing any of these approaches to give a product whose release characteristics provide the desired $C_{max}$, $T_{max}$, $C_{24h}$, $AUC_{0-t}$, and $AUC_{0-\infty}$ for any particular quantity of bexagliflozin.

Preferred tablets of the invention include bexagliflozin dispersed in a water-insoluble (e.g. wax) matrix (e.g. based on glyceryl dibehenate, as discussed below).

In addition to employing these techniques for providing extended release from the tablet, it is also desirable to adapt the tablet for gastric retention (as discussed below) to increase the proportion of the extended release which occurs in the duodenum, thereby further refining the in vivo pharmacokinetic behavior by delaying progress of bexagliflozin through the small intestine.

Before in vivo testing to determine $C_{max}$, $T_{max}$, $C_{24h}$, $AUC_{0-t}$, and/or $AUC_{0-\infty}$ in humans it can be useful to subject a tablet to in vitro dissolution testing to give some preliminary predictions and to facilitate design modifications. These in vitro tests are used in a regulatory setting to ensure that a tablet can reliably and safely deliver the required therapeutic amount of a drug into the bloodstream, and involve applying formal dissolution acceptance testing to tablets sampled from manufacturing batches intended to be delivered to human patients. Such formal acceptance testing ensures that the desired amount of bexagliflozin can be delivered in vivo over the desired time interval.

The invention therefore provides a solid oral dosage form (most typically an extended release tablet) that contains bexagliflozin and that, in an in vitro dissolution test in simulated gastric fluid (see below), releases ≤17% of its bexagliflozin after 1 hour and releases ≥80% after 8 hours. Thus, at least 83% of the bexagliflozin remains in the dosage form 1 hour into the in vitro dissolution test, but at least 80% has been released 8 hours into the test (which includes embodiments in which 100% has already been released at the 8-hour point). The amount of bexagliflozin released by this tablet after 1 hour in the dissolution test is less than with an immediate release capsule containing the same amount of bexagliflozin. In one embodiment, this dosage form releases between 20-45% (inclusive) of its bexagliflozin after 3 hours and between 45-75% (inclusive) of its bexagliflozin after 5 hours.

In embodiments of the invention where a dosage form (such as an extended release tablet) releases between 20-45% of its bexagliflozin after 3 hours in an in vitro dissolution test, the dosage form can be prepared such that it releases between 23-43% of its bexagliflozin after 3 hours.

In embodiments of the invention where a dosage form (such as an extended release tablet) releases between 45-75% of its bexagliflozin after 5 hours in an in vitro dissolution test, the dosage form can be prepared such that it releases (a) between 45-72% of its bexagliflozin after 5 hours (b) between 50-70% of its bexagliflozin after 5 hours (c) between 49-69% of its bexagliflozin after 5 hours or (d) between 48-68% of its bexagliflozin after 5 hours. More generally, the dosage form may release between x-y % of its bexagliflozin after 5 hours, where: x is selected from 45, 47, 48, 49, or 50; and y is selected from 68, 69, 70, 72 or 75.

In one embodiment, an extended release tablet may release in an in vitro dissolution test (1) between 23-43% of its bexagliflozin after 3 hours and (2) between 45-72%, between 50-70%, between 49-69%, or between 48-68%, of its bexagliflozin after 5 hours. These percentages may therefore be the criteria used at 3 hours and 5 hours in the in vitro dissolution testing disclosed herein.

Because determining these release characteristics is necessarily destructive, these parameters need not be determined directly for a particular tablet of interest, but rather for a tablet made by the same manufacturing process with the same components. Thus, a manufacturing batch of tablets can be made by a particular process, and in vitro dissolution testing is performed on a sample set of representative tablets from the manufacturing batch. If the results for this testing meet the requirements noted above then tablets made by the manufacturing process in question are tablets of the present invention. Thus the invention also provides the tablets from any such manufacturing batch.

The in vitro dissolution test which is used for these determinations is one of several that are standard in the art, particularly for extended release tablets e.g. see USP <711> Dissolution or Ph. Eur. 2.9.3. Further details are given below.

Studies of particular types of tablet formulations enable provision of an IVIVC (in vitro-in vivo correlation) that describes the relationship between an in vitro attribute of a tablet (e.g. the rate or extent of drug release) and a relevant in vivo response (e.g. $C_{max}$ or $AUC_{0\text{-}t}$). Models of this type facilitate the rational development, evaluation and modification of extended-release dosage tablets of the invention.

Ideally, an extended release preparation exhibits no dependence on prandial state, but if such an influence is unavoidable (for example, if the extended release mechanism depends on the mechanics of content release from the stomach as in the case of several embodiments of the present invention), then it is desirable that the consequences of prior food consumption be predictable and circumscribed, in any case not to present a risk to the patient of either an adverse side effect or an inadequate therapeutic effect. These criteria are met by tablets of the present invention.

Various medications are known to affect gastrointestinal mobility either as a side effect or as a mechanism of therapeutic action. Among the agents that influence gastric emptying and that are frequently co-delivered with oral antidiabetic drugs are agonists of the glucagon-like peptide-1 (GLP-1) receptor. GLP-1 receptor agonists suppress gastric emptying and have the potential to mimic the fed prandial state, thereby elevating exposure to bexagliflozin if delivered in advance of the bexagliflozin dose. At present, most GLP-1 receptor agonists are delivered by subcutaneous injection, but a preparation of semaglutide for oral delivery has been recently approved and more such agonist preparations or synthetic agonists may be approved in the future. As in the case of prandial state, it is desirable that the consequences of GLP-1 receptor agonist administration be predictable and circumscribed. These criteria are met by tablets of the present invention.

Gastric Retention

Extended release tablets having the desired $C_{max}$, $T_{max}$, $C_{24h}$, $AUC_{0\text{-}t}$, and/or $AUC_{0\text{-}\infty}$ properties can be prepared by following the guidance given above, in conjunction with common general knowledge about the preparation of extended release tablets. A further way to modify the tablets to achieve the desired parameters is to incorporate into the tablet a gastric retention adaptation, and in particular one or more of the four adaptations discussed below. The overall goal of gastric retention as discussed herein is to delay progress of bexagliflozin through the small intestine, thereby encouraging a large part of the extended release of bexagliflozin to occur in the stomach or high in the small intestine (see Hou et al. (2003) *Crit Rev Ther Drug Carrier Syst* 20:459-97). Compared to immediate release capsules these adaptations have all been shown to decrease in vivo plasma $C_{max}$ while still providing a therapeutically useful $C_{24h}$, and also with $T_{max}$, $AUC_{0\text{-}t}$, and $AUC_{0\text{-}\infty}$ within the desired ranges.

A first approach for achieving the desired in vivo pharmacokinetic behavior is to include an effervescent excipient in the tablet, and in particular an excipient that will effervesce on contact with gastric acid e.g. a carbonate or a bicarbonate or hydrogen carbonate salt, such as sodium bicarbonate. As the tablet effervesces it tends to float due to the release of gas, and thus the tablet's progress towards the pyloric sphincter at the base of the stomach is delayed (e.g. see Wei et al. (2001) *Drug Dev Ind Pharm* 27:469-74, Ray & Prusty (2010) *Int J Appl Pharmaceutics* 2:12-16). A bicarbonate-containing tablet matrix provides the additional advantage of protecting bexagliflozin against acid degradation. As shown in the examples, the inclusion of an effervescent excipient reduces $C_{max}$, thereby contributing to the desired pharmacokinetic profile.

A second approach for achieving the desired in vivo pharmacokinetic behavior is to construct the tablet so that on contact with gastric contents it disperses into a large number of granules or pellets, which in turn provide extended release. In general, it takes longer for the stomach to expel multiple small granules/pellets than one large tablet. A similar approach was disclosed by Aburahma & Hamza Yel (2011) *Pharm Dev Technol* 16(4):316-30, who compressed extended-release beads with a fast-disintegrating component.

A third approach for achieving the desired in vivo pharmacokinetic behavior is to use low density excipients that thereby provide a buoyant or floating tablet. By using adequate amounts of low density excipients, it is possible to provide a tablet with an overall density below that of gastric contents, thereby permitting it to float in the stomach and thus delay its transit to the pyloric sphincter without needing effervescence (e.g. Srikanth Meka et al. (2014) *Acta Pharm* 64:485-494). As shown in the examples, this approach provides a useful decrease in $C_{max}$. Gastric contents have a density of about 1.004-1.010 g/$cm^3$ and so the tablet should have a density below this, ideally such that it can float.

Buoyancy, and the length of time that a tablet remains buoyant as it degrades, can be assessed in vitro in simulated gastric fluids maintained at 37° C. In some embodiments, tablets of the invention may remain buoyant (i.e. persist on the surface) until they have released 90% of their bexagliflozin. In some embodiments, tablets of the invention may remain buoyant for 5 hours or more e.g. for 8 hours or more. In practice, the tablets can be studied using the same technique as discussed below for the in vitro dissolution test e.g. in an apparatus containing 900 mL of 0.1 N HCl at 37±0.5° C. (simulated gastric fluid). The density of a tablet can be determined by the displacement method using analytical grade benzene as a displacing medium.

A fourth approach for achieving the desired in vivo pharmacokinetic behavior is to include a mucoadhesive excipient in the tablet. Mucoadhesives permit the tablet to interact with the mucosal surfaces of the gastrointestinal tract, for example of the stomach wall, thereby retarding the tablet's progress. This approach is discussed in, for instance, Jha & Nanda (2013) *Asian J Biomed Pharm Sci* 3:44-49. Various mucoadhesive excipients suitable for inclusion in tablets are known in the art, and these are often hydrophilic polymers. In general, good mucoadhesives have strong hydrogen bonding groups (—OH, —COOH), strong anionic charges, sufficient flexibility to penetrate the extended glycan network of the cell glycocalyx, surface tension characteristics suitable for wetting mucus/mucosal tissue surface, and/or a high molecular weight (see Yadav et al. (2010) *J Chem Pharm Res* 2:418-32). Examples of mucoadhesive excipients are given below. Some mucoadhesives are known to provide tablets with extended release characteristics (e.g. HPMC, polyethylene oxides) and so can usefully fulfill both roles in a tablet of the invention. A useful amount of mucoadhesive in a tablet of the invention can be between 10-25% by weight of the total tablet.

Thus, the fourth aspect of the invention provides an extended release tablet that contains bexagliflozin and a mucoadhesive. The mucoadhesive is included in the tablet at an amount that retards its progress in vivo through the stomach and/or the duodenum when compared to an equivalent tablet that has the same composition except for the absence of the mucoadhesive. A preferred mucoadhesive for inclusion in tablets of the invention is a nonionic polyethylene oxide polymer, particularly with an average molecular weight of 800,000 g/mol or more e.g. from 900,000-5,000,000 g/mol. These hydrophilic polymer powders are available in pharmacopoeial grade under the trade name POLYOX™ from Dow Chemical, with molecular weights ranging from 100,000-7,000,000 g/mol. They are known as both mucoadhesives and for providing extended release characteristics and so they can usefully fulfill both roles in a tablet of the invention. Suitable quantities of mucoadhesive are discussed above.

The four approaches discussed above can be used individually to provide extended release tablets for delivery of bexagliflozin that display the desired pharmacokinetic parameters. In particular, each approach can decrease $C_{max}$ when compared to an immediate release formulation. The degree of the decrease can be controlled to a certain extent, in particular by increasing the particular adaptation, to provide a desired $C_{max}$ for any particular amount of bexagliflozin in the tablet. For instance, increasing amounts of an effervescent excipient or increasing the number of individual granules/pellets will, up to a point, increase gastric retention and thus decrease $C_{max}$ accordingly. Similarly, increases in buoyancy will increase gastric retention, although there are practical limits on how far buoyancy can be increased. Finally, increased levels of mucoadhesive, or the use of a stronger mucoadhesive, will increase gastric retention although, again, there are practical limits on a tablet's capacity for mucoadhesive content. Overall, however, a person skilled in the art of tablet formulation will be able to make and test tablets utilizing these approaches and to adapt them according to the desired pharmacokinetic properties.

Although the four approaches can be used individually, advantageously the various approaches can be combined.

The inventors have found that the first approach on its own can decrease $C_{max}$ as desired, but that these tablets can display significant inter-patient variability (in particular for $T_{max}$). Without wishing to be bound by theory, this behavior could arise if the tablet exits the stomach earlier than desired in some patients, after which it no longer experiences the acid-driven disintegrating forces of effervescence and so drug release and thus bioavailability decreases. To alleviate this problem, the first and second approaches can be combined e.g. by compressing multiple effervescent granules into a single tablet, with the individual effervescent granules being released as the tablet disperses in the stomach.

The second approach is technically difficult to implement consistently and, although it decreases $C_{max}$, the effect is not so great (e.g. not as much as the first approach). Furthermore, the granules can have a relatively short commercial shelf-life, so the second approach is not preferred, either on its own or in combination with any of the other approaches.

When more than one approach is used for improving the pharmacokinetic behavior, one option is to combine the third and fourth approaches to give a low-density tablet that includes a mucoadhesive. As shown in the examples, this combination of approaches provides tablets having advantageous properties for delivery of bexagliflozin in humans.

Thus, the invention provides an extended release tablet that contains bexagliflozin and a mucoadhesive, wherein the tablet has a density below that of human gastric acid. Further details of suitable mucoadhesives and their content, and also of suitable densities, are discussed above.

Gastric retention can be measured by including a radionuclide in the formulation and directly recording the fraction of the formulation that remains in the stomach as a function of time following dosing using an appropriate scintillation camera. Although this approach has relatively high precision, it has two principal drawbacks: (i) the radionuclide itself is typically not found in the commercial article and hence the formulation departs in its constitution from the intended commercial form, and (ii) the conduct of such experiments is difficult and expensive and subjects the participants to the additional risk of exposure to radioactivity. Thus, gastric retention can instead be determined by inference from other properties of a formulation e.g. by comparison of the $T_{max}$ produced by the formulation to the $T_{max}$ produced by an immediate release formulation, or by comparison of the $T_{max}$ in the fasted state to the $T_{max}$ in the fed state. As mentioned above, studies using [$^{14}$C]-bexagliflozin have shown that colonic absorption is minimal, and the majority of absorption takes place in the small bowel. The effect of prandial state is also consistent with this description. For example, bexagliflozin capsules in strengths from 6.7 to 34 mg produced a $T_{max}$ from 1 to 2 h in the fasted state, but 5 h in the fed state, which is explicable if release of the gastric contents were to be required for a maximal rate of absorption. Bexagliflozin extended release tablets of the U20 formulation (see below) produced a $T_{max}$ of 3.5 h in the fasted state and 5 h in the fed state, consistent with the view that they are retained in the stomach for a longer period of time than extended release formulations.

Tablet Components

As discussed above, a tablet of the invention will generally or optionally include, in addition to bexagliflozin: one or more release-controlling agents (such as ingredients for forming a matrix or a membrane); one or more matrix or membrane modifiers (such as channeling agents or wicking agents); one or more solubilizers; one or more glidants, lubricants and/or flow aids; one or more disintegrants; one or more fillers; one or more binders; one or more density modifiers and/or effervescent components; one or more colorings; one or more flavorings; one or more anti-oxidants; and/or one or more mucoadhesives. Such components will generally be present in admixture within the tablet, but may also be present in differing proportion in layers or discrete geometric structures, such as particles or spheres of one composition embedded in another, or in sheets or blocks of material of differing bulk composition.

It is common to create tablets that have a core of one composition surrounded by a coating or exterior layer of another. Tablets of the invention will typically include a coating.

Examples of release-controlling agents for forming a matrix include, but are not limited to, the water-swellable hydrophilic polymers (such as hydroxypropyl-celluloses or -methylcelluloses, sodium carboxymethylcelluloses, alginates, alginic acid, gelatin, xanthan gums (with or without locust bean gum), carbopols, polyethylene oxides, galactomannoses, etc.), waxes (such as hydrogenated vegetable oils, microcrystalline wax, carnauba wax, etc.), and insoluble polymers (e.g. ethylcelluloses). These components can make 15-40% by weight of the tablet.

A particularly useful release-controlling agent for forming a tablet matrix of the present invention is glyceryl dibehenate, as this advantageously has a density lower than gastric fluid and is resistant to gastric lipase. Glyceryl dibehenate is known for use as a sustained-release agent (e.g. as described by Opota et al. (2013) *Int J Pharm Tech Res* 5:622-8). A preferred tablet includes 30-35% by weight of glyceryl dibehenate. The term “glyceryl dibehenate” is the current preferred pharmaceutical description for commercial mixtures of glyceryl esters (including mono-, di- and tri-behenic esters) that are predominantly in the form of the diester. There are two regioisomers of glyceryl monobehenic ester and two regioisomers of glyceryl dibehenic ester. Previously the term “glyceryl behenate” had been used to describe the commercial mixture of esters, but this terminology had the disadvantage of suggesting that the composition was principally in the form of the monobehenic ester, which is inaccurate. Commercial preparations of glyceryl dibehenate contain 40-60% by weight of the diester within the mixture. Any reference to “glyceryl dibehenate” herein should be understood to refer to products comprising a mixture of glyceryl esters of behenic acid, and not to the amount of glyceryl dibehenic ester contained therein.

Commercial preparations of glyceryl dibehenate may have been formulated to improve their performance in drug manufacturing processes, for example to improve blending or flow characteristics, and the inventors have found that formulations which have been micronized or atomized (such as COMPRITOL 888 ATO™) can have favorable properties for preparing tablets of the present invention.

Examples of release-controlling agents for forming a membrane include, but are not limited to, ethylcellulose, acrylic polymers (e.g. EUDRAGIT RL & RS™), shellac, and zein. These can be combined with plasticizers such as dibutyl phthalate, diethyl phthalate, dibutyl sebecate, or citric acid esters. A plasticizer will generally be included at about 10-25% by weight of the membrane polymer, giving enough for complete coalescence of the membrane to form a film without making it too elastic, plastic, soft or permeable.

Examples of matrix modifiers include, but are not limited to, sugars, polyols and soluble salts. These can modify the diffusional characteristics of the matrix, and also the rate and extent of its hydration, and thus modify bexagliflozin release. Channeling agents include sodium chloride, sugars, and polyols (e.g. lactose), and these agents can make 10-30% by weight of the tablet.

Examples of solubilizers include, but are not limited to, surfactants (including ionic and non-ionic surfactants) such as sodium lauryl sulfate, cetyltrimethylammonium bromide, polysorbates (such as polysorbate 20 or 80), poloxamers (such as poloxamer 188 or 207), and macrogols. A preferred tablet includes a poloxamer, which is ideally micronized e.g. in micro-prilled form (EP-A-1661558). An average poloxamer particle size of between 10-200 μm is useful. The most preferred poloxamer is poloxamer 188 micronized. A preferred amount of poloxamer 188 in a tablet of the invention is 10-12% by weight. Higher levels of poloxamer can favor faster release from a tablet.

In some embodiments, a surfactant can be combined with amorphous bexagliflozin in the manner disclosed in WO2018/167589, with the aim of providing tablets having extended stability and good bioavailability (and, optionally, being bioequivalent to a reference tablet as disclosed herein). Useful surfactants for such embodiments are available under the trade names SEPITRAP™ 80 and DUBCARE™ GPE810. SEPITRAP™ 80 is a micro-encapsulated form of polysorbate 80 in powder form, in which polysorbate 80 is adsorbed onto a porous magnesium aluminometasilicate carrier. DUBCARE™ GPE810 is a mixture of PEG-8 caprylic/capric glycerides.

Examples of lubricants, glidants and flow aids include, but are not limited to, magnesium stearate, calcium stearate, stearic acid, hydrogenated vegetable oil, glyceryl palmitostearate, glyceryl dibehenate, sodium stearyl fumarate, colloidal silicon dioxide, and talc. The amount of lubricant in a tablet can generally be between 1-5% by weight. Preferred tablets of the invention include magnesium stearate and/or colloidal silicon dioxide (e.g. an amorphous anhydrous form). A preferred tablet includes 1.5-2.5% by weight magnesium stearate and/or 1.0-1.5% by weight colloidal silicon dioxide.

Examples of disintegrants include, but are not limited to, starches, celluloses, cross-linked PVP, sodium starch glycolate, croscarmellose sodium, etc.

Examples of fillers (also known as bulking agents or diluents) include, but are not limited to, starches, maltodextrins, polyols (such as lactose), and celluloses. Preferred tablets of the invention include lactose and/or microcrystalline cellulose (e.g. the Avicel range of products; see Doelker et al. (1995) *Drug Dev Ind Pharmacy* 21:643-61). Lactose can be used in anhydrous or hydrated form (e.g. monohydrate), and is typically prepared by spray drying, fluid bed granulation, or roller drying. Preferred microcrystalline celluloses have a particle size between about 150-200 μm. A preferred tablet includes 11-13% by weight lactose and/or 18-20% by weight microcrystalline cellulose. Spray-dried lactose monohydrate is preferred.

Examples of binders include, but are not limited to, cross-linked PVP, HPMC, microcrystalline cellulose, sucrose, starches, etc.

Examples of effervescent components include, but are not limited to, carbonate or bicarbonate (hydrogen carbonate) salts, such as sodium bicarbonate.

Examples of antioxidants include, but are not limited to, butylated hydroxyanisole, butylated hydroxytoluene, sodium metabisulfite, propyl gallate, and cysteine. Preferred tablets include butylhydroxytoluene as an anti-oxidant.

Examples of mucoadhesives include, but are not limited to, carbopols (polymers of acrylic acid cross-linked with polyalkenyl ethers or divinyl glycol), cross-linked carboxy-polymethylenes, carboxy-methylcelluloses (such as sodium carboxy methylcellulose), hydroxy-ethylcellulose, hydroxy-propyl-methylcellulose, polycarbophils, gum tragacanth, poly(acrylic acid/divinyl benzene), alginates (such as sodium alginate), gum karaya, and polyoxyethylenes (also known as polyethylene oxides or polyethylene glycols). As mentioned above, a useful amount of mucoadhesive in a tablet of the invention can be between 10-25% by weight of the total tablet. A preferred mucoadhesive component for inclusion in a tablet of the invention is a nonionic polyethylene oxide polymer, particularly with an average molecular weight (e.g. number average) of at least 800,000 g/mol (based on rheological measurements). A preferred tablet includes 16-20% by weight of polyethylene oxide.

Although uncoated tablets may be used, it is more usual to provide a coated tablet, in which case a conventional non-enteric coating may be used. The coating may be white or colored e.g. blue. Suitable coatings include, but are not limited to, polymeric film coatings such as those comprising polyvinyl alcohol e.g. ‘OPADRY II’™ (which includes part-hydrolyzed PVA, titanium dioxide, macrogol 3350 and talc, with optional coloring such as indigo carmine or iron oxide yellow or FD&C yellow #6). The amount of coating will generally be between 2.5-3.5% of the core’s weight.

Some components can play multiple roles in tableting e.g. glyceryl dibehenate can be used as a release-controlling agent in a tablet matrix or as a gastroretentive excipient (by virtue of its density), or as a lubricant, and polyethylene oxide can be used as a release-controlling agent or it can be used as a mucoadhesive. Thus, a single component can play multiple roles within a single tablet, but often a component will be included with a single aim and so its quantity and location (in the tablet and/or in the manufacturing process) will be selected accordingly.

Tablets of the invention will generally have a hardness within the range 20 to 100 N, and more typically between 20-60 N, 30-40 N, or 60-90 N. Hardness can conveniently be assessed using the Dr. Schleuniger Pharmatron tester which drives an anvil to compress a tablet at a constant rate until it fractures, operating in accordance with USP <1217>.

Tablets of the invention will generally have a friability of ≤1% by weight. Friability can be assessed according to USP <1216>.

Tablets of the invention will generally have a water content of 55% by weight. Water content can be assessed according to USP <921>.

Tablets of the invention can conveniently be prepared by direct compression (followed, if required, by coating).

Preferred Tablets

Preferred tablets of the invention comprise: bexagliflozin; glyceryl dibehenate; polyethylene oxide; lactose (anhydrous or, preferably, monohydrate); poloxamer 188 (preferably micronized); microcrystalline cellulose; colloidal silicon dioxide; and magnesium stearate; optionally also having a coating comprising polyvinyl alcohol.

Examples of such tablets have the following composition per tablet: bexagliflozin, between 3-60 mg; glyceryl dibehenate, between 100-140 mg; polyethylene oxide, between 50-75 mg; lactose, between 40-50 mg; poloxamer 188, between 40-45 mg; microcrystalline cellulose, between 60-80 mg; colloidal silicon dioxide, between 4-5 mg; and magnesium stearate, between 6-9 mg; optionally also having 10-12 mg of a coating which comprises polyvinyl alcohol.

Three preferred tablets of the invention comprise one of the following cores, for which further details of the excipients are well known, and can also be found in *Handbook of Pharmaceutical Excipients* (eds. Sheskey, Cook & Cable; 8th edition 2016):

| | (i) | (ii) | (iii) |
|---|---|---|---|
| Bexagliflozin | 5 mg | 10 mg | 20 mg |
| Polyethylene oxide, average molecular weight 900,000 | 65 mg | 65 mg | 65 mg |
| Glyceryl dibehenate | 120 mg | 120 mg | 120 mg |
| Lactose (either anhydrous or monohydrate e.g. spray-dried) | 45 mg | 45 mg | 45 mg |
| Poloxamer 188 | 42 mg | 42 mg | 42 mg |
| Microcrystalline cellulose | 70 mg | 70 mg | 70 mg |
| Colloidal silicon dioxide | 4.5 mg | 4.5 mg | 4.5 mg |
| Magnesium stearate | 7.5 mg | 7.5 mg | 7.5 mg |

The core preferably has a hardness of between 40-60 N or 60-90 N, and a friability of ≤1% by weight.

The invention also provides a tablet comprising one of these three cores coated with a polymeric film coating comprising polyvinyl alcohol, titanium dioxide, and macrogol 3350. The amount of coating can be 3% of the core's weight.

In these preferred tablets: the poloxamer 188 should be micronized; the lactose can be anhydrous but is preferably a monohydrate; and the optional coating can comprise polyvinyl alcohol, titanium dioxide, macrogol 3350, talc, brilliant blue FCF and indigo carmine, such as an Opadry II blue product.

The invention also provides an oral dosage form (and in particular a solid oral dosage form, such as a tablet) that produces in a cohort of healthy subjects a geometric mean $C_{max}$ and geometric mean $AUC_{0-t}$ for which the 90% confidence intervals of the log-transformed $C_{max}$ and log-transformed $AUC_{0-t}$ fall, upon exponentiation, completely within the range 80.00-125.00% of the geometric mean $C_{max}$ and geometric mean $AUC_{0-t}$, respectively, of the values produced in the same cohort by a reference tablet having one of the following compositions (see also tablets U5, U10 and U20 below):

(a) A tablet having: a core consisting of an admixture of 5 mg bexagliflozin, 65 mg non-ionic polyethylene oxide having an average molecular weight of approximately 900,000 g/mol, 120 mg glyceryl dibehenate powder, 45 mg spray-dried lactose monohydrate, 42 mg micronized poloxamer 188, 70 mg microcrystalline cellulose, 4.5 mg amorphous anhydrous colloidal silicon dioxide, and 7.5 mg magnesium stearate; and a film coating consisting of 10.77 mg of a mixture of PVA, titanium dioxide, macrogol 3350, talc, brilliant blue FCF and indigo carmine (such as OPADRY II™ blue 85F99153); where the core has a tablet hardness of between 40-60 N and is formed by compression using a 14.8×6.5 mm caplet-shaped tablet punch.

(b) A tablet having: a core consisting of an admixture of 10 mg bexagliflozin, 65 mg non-ionic polyethylene oxide having an average molecular weight of approximately 900,000 g/mol, 120 mg glyceryl dibehenate powder, 45 mg spray-dried lactose monohydrate, 42 mg micronized poloxamer 188, 70 mg microcrystalline cellulose, 4.5 mg amorphous anhydrous colloidal silicon dioxide, and 7.5 mg magnesium stearate; and a film coating consisting of 10.92 mg of a mixture of PVA, titanium dioxide, macrogol 3350, talc, brilliant blue FCF and indigo carmine (such as OPADRY II™ blue 85F99153); where the core has a tablet hardness of between 40-60 N and is formed by compression using a 14.8×6.5 mm caplet-shaped tablet punch.

(c) A tablet having: a core consisting of an admixture of 20 mg bexagliflozin, 65 mg non-ionic polyethylene oxide having an average molecular weight of approximately 900,000 g/mol, 120 mg glyceryl dibehenate powder, 45 mg spray-dried lactose monohydrate, 42 mg micronized poloxamer 188, 70 mg microcrystalline cellulose, 4.5 mg amorphous anhydrous colloidal silicon dioxide, and 7.5 mg magnesium stearate; and a film coating consisting of 11.22 mg of a mixture of PVA, titanium dioxide, macrogol 3350, talc, brilliant blue FCF and indigo carmine (such as OPADRY II™ blue 85F99153); where the core has a tablet hardness of between 40-60 N and is formed by compression using a 14.8×6.5 mm caplet-shaped tablet punch.

These reference tablets (a), (b) and (c) can be manufactured as follows: (i) blending the bexagliflozin, colloidal silicon dioxide and 80% of the MCC and then sifting the mixture; (ii) add the remaining MCC to give mixture 'A'; (iii) sifting the polyethylene oxide, glyceryl dibehenate and lactose to give mixture 'B'; (iv) blending mixtures 'A' and 'B' together; (v) adding sifted magnesium stearate, followed by further blending; (vi) compressing this material into tablet cores e.g. using 14.8×6.5 mm caplet-shaped punches and appropriate dies; (vii) de-dusting; and (viii) coating e.g. using a 12% or 18% w/w suspension of the coating material to achieve a coating that results in an approximate increase in tablet mass of 3%. The bexagliflozin preparations used to manufacture these reference tablets should have the solid crystalline form disclosed in WO2011/153953. Preferred embodiments of such preparations have a particle size distribution having a d(0.9) ≤700 μm.

Further details for assessing whether the 90% confidence intervals of log-transformed $C_{max}$ and $AUC_{0-t}$ values fall within the 80.00-125.00% range of values achieved with the reference tablets are given in the next section e.g. the use of a random crossover study in a suitable test population, etc.

Bioequivalence

The invention thus provides oral dosage forms which are bioequivalent to reference tablets (a) to (c). The oral dosage form will include the same molar amount of bexagliflozin as the relevant reference tablet i.e. the same amount as 5 mg, 10 mg, or 20 mg of bexagliflozin of formula (I).

It is well known in the bioavailability and bioequivalence arts how to determine whether any particular tablet meets regulatory requirements for equivalent bioavailability and pharmacokinetic bioequivalence e.g. see: Niazi (2014) *Handbook ofBioequivalence Testing,* $2^{nd}$ Edition, ISBN 978-1482226379*; FDA Guidance for Industry: Bioequivalence Studies with Pharmacokinetic Endpoints for Drugs Submitted Under an ANDA*, December 2013*; FDA Guidance for Industry: Bioavailability and Bioequivalence Studies Submitted in NDAs or INDs—General Considerations*, March 2014*; FDA Guidance for Industry: Bioanalytical Method Validation*, May 2018*; Guideline On The Investigation Of Bioequivalence*, EMA January 2010 (CPMP/EWP/QWP/1401/98 Rev. 1/Corr **); and *Guideline on the pharmacokinetic and clinical evaluation of modified release dosage forms*, EMA November 2014 (EMA/CPMP/EWP/280/96 Corr1).

Many factors that vary from individual to individual can affect the concentration of a drug in plasma. It is therefore common to take into account the mass of the subject, whether the drug is administered in the fasted or fed state, the degree of impairment of hepatic and/or renal function of the subject, the subject's concomitant medications, diet, alcohol or tobacco consumption, and sex, racial, genetic and cultural influences. As such, drug concentrations can vary substantially from individual to individual, even under optimally controlled conditions. The specification of the properties of an extended release formulation are most precisely made by reference to attributes that can be measured in vitro, such as the percent dissolution as a function of time (see elsewhere herein). When reference is made to properties that are measured in vivo, it is appropriate to adjust or normalize the effects to the expected behavior in a well-characterized prototypical subject.

From a practical perspective, though, even the specification of a prototypical subject cannot capture all of the variation between individuals, and for this reason, comparisons between formulations are typically performed by administering to the same individual each of the formulations to be compared, for example the reference formulation on one day and the comparator formulation on another, and vice versa. Usually a substantial period of time (at least ten half-lives of the drug from the preceding formulation) is allowed to elapse so that prior administration of one formulation has little likelihood of affecting measurements made after the administration of the subsequent formulation. Because substantial inter-individual variation is nearly always present, the comparisons are usually made on groups of individuals, typically no fewer than 12. When certain criteria are met for the comparison of the pharmacokinetic measurements between the subjects who had received each of the two formulations, the formulations are said to be bioequivalent.

There are in principle many ways to define bioequivalence between formulations but a prevalent standard for regulatory purposes that is adopted herein is that two preparations can be considered bioequivalent for a particular pharmacokinetic parameter if the lower bound of the 90% confidence interval for the logarithm of the geometric mean for the parameter for a test formulation yields a value upon exponentiation that is ≥80.00% of the geometric mean for the same parameter for the reference formulation and if the upper bound of the 90% confidence interval for the logarithm of the geometric mean of the parameter for the test formulation yields a value upon exponentiation that is ≤125.00% of the geometric mean for the parameter for the reference formulation. The typical parameters that must be found to be meet this test are the observed maximum drug concentration ($C_{max}$), the area under the curve for the concentration as a function of time from the beginning of dosing to the last accurately measurable value ($AUC_{0-t}$) and the area under the curve for the concentration as a function of time from the beginning of dosing, extrapolated to infinite time ($AUC_{0-\infty}$). Geometric means and logarithms are used in these calculations because most physiological variables, including drug plasma concentrations, typically show a log-normal distribution on repeated sampling of the same individual, and on sampling from different individuals within a population.

The invention therefore provides an extended-release tablet comprising bexagliflozin, wherein the tablet is bioequivalent by $C_{max}$ and $AUC_{0-t}$ with any one of reference tablets (a) to (c).

To ensure statistical power a study to measure the $C_{max}$ and $AUC_{0-t}$ values will be performed in multiple subjects e.g. in a group of at least 12 (and normally between 24 and 36) healthy human adults.

For establishing bioequivalence a two-period, two-sequence, two-treatment, single-dose, crossover study design can be used, a single-dose parallel study design, or a replicate study design. The preferred design is a two-period, two-sequence, two-treatment, single-dose, crossover study using healthy subjects. Each study subject should receive each treatment (test and reference drug) in random order. The most accurate, sensitive and reproducible method of measuring the drug concentration in plasma should be used. For bexagliflozin the preferred method is a validated high performance or ultra high performance liquid chromatographic separation with detection of the analyte by a tandem mass spectrometry method. For an extended release bexagliflozin tablet, both a fasting bioequivalence study and a fed bioequivalence study should be conducted. In each case the highest dosage strength formulation should be tested. Multiple dose (e.g., steady state) studies are not recommended.

A minimum of 12 subjects with evaluable data are generally required to support a determination of bioequivalence. For a study conducted in the fasted prandial state, a minimum fast of 10 h before dosing is required and water should be withheld from 1 h before to 1 h after dosing. Food should not be provided for at least 4 h following dosing. The investigational product can be provided with 240 mL of water.

For a study conducted in the fed prandial state, a minimum fast of 10 h should precede a standard high fat, high calorie meal of 800 to 1000 kcal, with approximately 150, 250, and 500-600 kcal from protein, carbohydrate and fat, respectively (see e.g., *FDA Guidance for Industry:*

*Bioequivalence Studies with Pharmacokinetic Endpoints for Drugs Submitted Under an ANDA* (2013) and *Guideline on the pharmacokinetic and clinical evaluation of modified release dosage forms* (*EM*4/*CPMP*/*EWP*/280/96 *Corr*1) section 5.1.4.1.) The meal should be consumed in 30 minutes or less, and drug administration should be performed 30 min after the beginning of the meal. No additional food should be provided for a minimum of 4 h.

For testing in either prandial state venous blood specimens should be drawn at appropriate intervals, generally consisting of 12 to 18 specimens in total, and covering at least three terminal elimination half-lives of the drug. Dense sampling around the expected $T_{max}$ is recommended to provide the most accurate $C_{max}$.

Because determining the $C_{max}$ and $AUC_{0-t}$ values necessarily consumes each tablet tested, and because variation would be present from one test to the next, even if the tablets were identical in all respects and the same subject were used, the pharmacokinetic parameters are determined for an average of the $C_{max}$ and AUC values of a collection of subjects dosed with a representative sample set of tablets from a manufacturing batch. The average is composed geometrically instead of arithmetically. To take the $C_{max}$ as an example in this and the following, for a cohort of six subjects, the geometric mean $C_{max}$ is calculated as the sixth root of the product of the six $C_{max}$ values for the subjects. The same result will be obtained if the arithmetic average of the logarithms of the $C_{max}$ values is exponentiated. The values for the logarithms of the $C_m$ for each subject will collectively create a distribution of individual logarithms of $C_m$ values.

To compare a second manufacturing batch to the first, the measurement process can be repeated with the same subjects but with tablets from the second manufacturing batch. (In actual practice, the order of administration would typically be randomly chosen for each subject, so that some would receive tablets from the second manufacturing batch first and some from the first manufacturing batch first.) For each subject a difference is calculated by subtracting the logarithm of the $C_{max}$ for the tablet from the first manufacturing batch from the logarithm of the $C_{max}$ for the tablet from the second manufacturing batch. The exponential of this difference is the ratio of the $C_{max}$ for the second tablet to the $C_{max}$ for the first tablet, which is unity if the difference is zero ($e^0=1$). Following the usual statistical methods for analyzing differences between two collections of values (analysis of variance), the endpoints of the 90% confidence interval for the differences of the logarithms are determined. For the two distributions to be considered bioequivalent, the endpoints of the 90% confidence interval for the differences of the logarithms must fall between −0.22314 and +0.22314. If these values are exponentiated they give 80.00% and 125.00% respectively (e.g., $e^{-0.22314}=0.8000$).

Although it is considered advantageous to dose each subject with tablets from each manufacturing batch to minimize variation between the measured values, if different cohorts of subjects are used for evaluating the tablets from the two manufacturing batches a similar approach can be used in which the mean difference in the logarithms for the two cohorts is calculated and a 90% confidence interval for the differences of the logarithms is constructed.

This type of test can be applied to establish whether tablets in question are tablets as defined herein. If a batch of tablets made by an unknown manufacturing process is compared by the methodology described above to a batch of tablets of the present invention defined by reference to $C_{max}$ and $AUC_{0-t}$, and for both the $C_{max}$ and the $AUC_{0-t}$ the endpoints of the 90% confidence interval for the differences of the logarithms of the values for the two batches falls between −0.22314 and +0.22314, the batch of tablets made by the unknown process are tablets which meet the relevant $C_{max}$ and $AUC_{0-t}$ requirements.

A corollary of the above is that if a cohort of subjects is dosed twice with tablets of the present invention from the same manufacturing batch, and defined by reference to $C_{max}$ and $AUC_{0-t}$, the endpoints of the 90% confidence interval for the differences of the logarithms between the values for the first and second dosings for both the $C_m$ and the $AUC_{0-t}$ will fall between −0.22314 and +0.22314.

This can be expressed more formally to state that two representative sample sets from the same batch will produce in a cohort of healthy subjects an inter-set mean difference in the logarithm of the $C_{max}$ and the logarithm of the $AUC_{0-t}$ for which the endpoints of the 90% confidence interval for the inter-set differences of the logarithms falls between −0.22314 and +0.22314. The distinction from the preceding paragraph is that the order of testing from the two sample sets may be randomly assigned among the subjects of the cohort, as for example is recommended in bioequivalence testing regulatory guidance documents.

In Vitro Dissolution Testing

Methods for the testing of extended release solid oral dosage forms are well known in the art and include USP <711>, which specifies the types of apparatus as well as the methods for use for immediate and extended release solid oral dosage forms.

Testing for bexagliflozin extended release tablets is conducted in USP Apparatus 1 (a basket apparatus e.g. with a nominal capacity of 1 liter), charged with 900 mL of 0.1 N HCl (i.e. simulated gastric fluid) and stirred at a rate of 50 rpm with the temperature maintained at 37±0.5° C. Individual tablets are placed in the apparatus and sampling conducted at the specified times (e.g. 1, 3, 5 and 8 h) by withdrawal of 10 mL of fluid without replacement. At each timepoint the concentration of bexagliflozin in the fluid sample is determined (e.g. by a validated HPLC method), thereby permitting calculation of the amount which has been released from a tablet. Where such a method involves filtering the withdrawn fluid before HPLC analysis, to avoid variation caused by possible interaction of bexagliflozin with the filter (e.g. with a PVDF material) it can be useful to filter a first fraction of the fluid (e.g. 3.5 mL of a 10 mL sample) and then to perform analysis on a subsequent fraction (e.g. on the remaining 6.5 mL of the 10 mL sample).

Testing can proceed in up to three stages, referred to as levels. In the first stage (level one testing), six tablets are analyzed. A success is recorded if no individual value lies outside each of the stated ranges and no individual value is less than the stated amount at the final test time. If this criterion is not met, an additional 6 tablets are analyzed (level two testing). A success is recorded if the average value of all 12 units lies within each of the stated ranges (i.e. for 1, 3, 5 and 8 h) and is not less than the stated amount at the final test time AND if none is more than 10% of the labelled amount (i.e. 2 mg for a 20 mg tablet) outside each of the stated ranges and none is more than 10% of the labelled amount below the stated amount at the final test time. If the level two criteria are not met, level three testing must be undertaken. An additional 12 tablets are tested. The average of all 24 tablets must lie within each of the stated ranges and not be less than the stated amount at the final test time. Not more than 2 of the 24 units are more than 10% of labelled content outside each of the stated ranges; not more than 2 of the 24 units are more than 10% of labelled content below the stated amount at the final test time; and none of the units is more than 20% of labelled content (i.e. 4 mg for a 20 mg tablet) outside each of the stated ranges or more than 20% of labelled content below the stated amount at the final test time.

A manufacturing batch of bexagliflozin extended release tablets is said to have passed formal dissolution acceptance testing if the criteria for success for at least one of the three testing levels is satisfied. Representative units of the manufacturing batch will meet these criteria, as defined in Acceptance Table 2 of USP <711>. In practical terms, testing is terminated once a success has been achieved. Additional testing, for example repeat testing to begin anew at level one if testing fails at level three, should not be performed.

The invention thus provides an extended-release tablet comprising bexagliflozin, wherein the tablet is from a manufacturing batch having a composition or method of testing or manufacture that falls within the formal acceptable ranges for process, testing or ingredient variation of the U5, U10, U20 or U40 formulations (see below). Of these four formulations, U20 is the most preferred for use in diabetes therapy.

The invention also provides an extended-release tablet comprising bexagliflozin, wherein the tablet is from a manufacturing batch having the composition of the U5, U10, U20 or U40 formulations (see below).

Similarly, the invention provides a solid oral dosage form (and in particular a tablet, such as an extended release tablet) that contains bexagliflozin and that in an in vitro dissolution test in simulated gastric fluid has a $f_2$ value of >50 when compared to one of reference tablets (a), (b) or (c) as defined above, wherein $f_2$ is the decimal logarithmic reciprocal square root transformation of the sum of the squared error:

$$f_2 = 100 - 25\ \log_{10}\left(1 + n^{-1}\sum_{i=1}^{n}(R_i - T_i)^2\right)$$

where: n is number of time points at which dissolution is measured; $R_i$ is the dissolution percentage of the reference tablet at the i-th timepoint; and $T_i$ is the dissolution percentage of the solid oral dosage form at the i-th timepoint.

The invention provides an extended release tablet that contains bexagliflozin and that, in an in vitro dissolution test in simulated gastric fluid, releases ≤17% of its bexagliflozin after 1 hour and releases ≥80% after 8 hours. Preferably, this tablet releases between 20-45% of its bexagliflozin after 3 hours, and/or between 45-75% of its bexagliflozin after 5 hours. As mentioned above, within the 45-75% range after 5 hours it is possible for a tablet to release (a) between 45-72% of its bexagliflozin (b) between 50-70% of its bexagliflozin (c) between 49-69% of its bexagliflozin or (d) between 48-68% of its bexagliflozin. Furthermore, within the 20-45% range after 3 hours, it is possible for a tablet to release between 23-43% of its bexagliflozin.

The invention also provides a solid oral dosage form, typically an extended release tablet, that contains bexagliflozin and that passes formal dissolution acceptance testing (see above) in simulated gastric fluid with criterion standards for release of ≤17% of the bexagliflozin dosage after 1 hour and >80% of the bexagliflozin after 8 hours. Preferably, the criterion standard for dissolution acceptance testing requires that between 20-45% of the bexagliflozin be released after 3 hours (e.g. between 23-43%) and/or between 45-75% of the bexagliflozin be released after 5 hours (e.g. between 45-72%, 50-70%, 49-69%, or 48-68%, as mentioned above). In the formal dissolution acceptance testing, these dosage forms pass at least one level of a formal three level testing protocol as defined by USP <711> Acceptance Table 2.

Therapeutic Methods

Tablets of the invention may be used to treat diabetes and its symptoms, and in particular type 2 diabetes. More specifically, tablets of the invention may be used as an adjunct to diet and exercise to improve glycemic control in adults with type 2 diabetes mellitus.

The invention provides methods for treating subjects suffering from diabetes or its symptoms. The methods involve administering a tablet of the invention to the subject, and will generally involve repeated administrations (e.g. once daily), either indefinitely or until a desired therapeutic result is achieved. A dose of 5 mg, 10 mg, 20 mg or 40 mg bexagliflozin once daily is typical.

Similarly, the invention provides a tablet of the invention for use in such treatment methods.

The invention also provides the use of bexagliflozin and at least one pharmaceutically acceptable excipient in the manufacture of a medicament for treating diabetes, wherein the medicament is a tablet of the invention as discussed above. The pharmaceutically acceptable excipient(s) can be selected as discussed herein to provide an extended release tablet of the invention.

As discussed above, a single tablet of the invention preferably includes 5 mg, 10 mg, 20 mg, or 40 mg of bexagliflozin. Thus, methods and uses of the invention will generally involve administering to the subject 5 mg, 10 mg, 20 mg, or 40 mg (or an integer multiple thereof) of bexagliflozin e.g. 5 mg, 10 mg, 20 mg, or 40 mg once daily.

These therapeutic methods and uses may be performed on a diabetic subject who is also receiving a second diabetes therapy, such as a GLP-1 receptor agonist (e.g. exenatide, lixisenatide, dulaglutide, liraglutide, albiglutide or semaglutide). As discussed elsewhere herein, tablets of the invention can be safely administered to such subjects, without requiring a change in prescribing pattern.

Among the existing GLP-1 receptor agonists can be counted exenatide, lixisenatide, liraglutide, albiglutide, dulaglutide and semaglutide (reviewed by Gentilella et al., (2019) *Diabetes Metab Res Rev* 35:e3070 doi: 10.1002/dmrr.3070). The first two are analogs of exendin-4, a peptide isolated from the saliva of Gila monsters that facilitates predation by causing severe hypoglycemia in bitten prey. The latter four are analogs of human GLP-1 with modifications that extend plasma half-life. Approved dosages of these agonists are as follows: exenatide is delivered in 5 g or 10 g subcutaneous injections, twice daily, or by once weekly injection of an extended release depot preparation; lixisenatide is delivered by 20 g once daily subcutaneous injection; in maintenance therapy liraglutide is delivered once daily by subcutaneous injection of 1.2 or 1.8 mg; the others are delivered by weekly subcutaneous injection, albiglutide in 30 or 50 mg dosage, dulaglutide in 0.75 or 1.5 mg dosage, and semaglutide in 0.5 or 1.0 mg dosage.

MODES FOR CARRYING OUT THE INVENTION

Example 1—Effervescent Tablets

Effervescent tablets containing 10, 15, or 20 mg bexagliflozin were developed. Early tablets were formed by direct compression and were composed of hydroxypropyl-methylcellulose (HPMC; low and medium viscosity), lactose monohydrate, sodium bicarbonate, and magnesium stearate. Each of these excipients had first been shown to be compatible with bexagliflozin during stability studies (whereas, for instance, breakdown was observed when citric acid monohydrate was tested as an effervescence agent). Bexagliflozin and the lactose monohydrate (diluent) were mixed and sieved, and then HPMC, sodium bicarbonate and silicon dioxide were added in a blender. Finally, the magnesium stearate was added as a lubricant and the tablets were formed.

Two target release profiles were initially proposed, to release ≥80% of bexagliflozin either at 12 hours or at 18 hours, as assessed by an in vitro dissolution test of the tablets (USP Apparatus 2, 50 rpm at 37±0.5° C., with sinkers) in 900 mL of 0.1 N HCl. The tablet compositions were as follows:

| Component | Mass (mg) | % wt | Mass (mg) | % wt |
|---|---|---|---|---|
| Bexagliflozin | 10 | 6.67% | 10 | 6.67% |
| HPMC (low viscosity) | 35 | 23.33% | 37.5 | 25% |
| HPMC (medium viscosity) | 10 | 6.67% | — | — |
| Lactose monohydrate | 78.5 | 52.33% | 86 | 57.33% |
| Sodium bicarbonate | 15 | 10% | 15 | 10% |
| Magnesium stearate | 1.5 | 1% | 1.5 | 1% |
| Total | 150 | 100% | 150 | 100% |

The tablet with a mixture of HPMCs showed 68% release at 10 hours and 82% at 14 hours. In contrast, the tablet with a single HPMC showed 62% release at 10 hours, 75% at 12 hours, and 89% at 16 hours.

Two further batches were prepared:

| Component | Mass (mg) | % wt | Mass (mg) | % wt |
|---|---|---|---|---|
| Bexagliflozin | 10 | 6.67% | 10 | 6.67% |
| HPMC (low) | 40.5 | 27% | 28.125 | 18.75% |
| HPMC (medium) | — | — | 9.375 | 6.25% |
| Lactose monohydrate | 83 | 55.33% | 86 | 57.33% |
| Sodium bicarbonate | 15 | 10% | 15 | 10% |
| Magnesium stearate | 1.5 | 1% | 1.5 | 1% |
| Total | 150 | 100% | 150 | 100% |

These two tablets had similar release profiles until 12 hours (750%), but thereafter release was slightly quicker using the mixture of HPMCs (91% vs. 87% at 18 hours).

Various further tablets were prepared, and a final tablet composition was selected as follows:

| Component | Mass (mg) | % wt |
|---|---|---|
| Bexagliflozin | 10 | 6.67% |
| HPMC (low) | 37.5 | 25% |
| Lactose monohydrate | 86 | 57.33% |
| Sodium bicarbonate | 15 | 10% |
| Magnesium stearate | 1.5 | 1% |
| Total | 150 | 100% |

Different formulations were initially tested for 20 mg tablets:

| Component | Mass (mg) | % wt | Mass (mg) | % wt |
|---|---|---|---|---|
| Bexagliflozin | 20 | 13.33% | 20 | 13.33% |
| HPMC (low) | 45 | 30% | 30 | 20% |
| HPMC (medium) | — | — | 15 | 10% |
| Lactose monohydrate | 67.75 | 45.17% | 67.75 | 45.17% |
| Sodium bicarbonate | 15 | 10% | 15 | 10% |
| Colloidal silicon dioxide | 0.75 | 0.5% | 0.75 | 0.5% |
| Magnesium stearate | 1.5 | 1% | 1.5 | 1% |
| Total | 150 | 100% | 150 | 100% |

These tablets had a slower release profile than desired (less than 7500 after 12 hours in both cases), so modifications were made. Final tablet compositions for 15 mg and 20 mg tablets were selected as follows:

| Component | Mass (mg) | % wt | Mass (mg) | % wt |
|---|---|---|---|---|
| Bexagliflozin | 20 | 13.33% | 15 | 10% |
| HPMC (low) | 37.5 | 25% | 37.5 | 25% |
| Lactose monohydrate | 76 | 50.67% | 81 | 54% |
| Sodium bicarbonate | 15 | 10% | 15 | 10% |
| Colloidal silicon dioxide | 0.75 | 0.5% | 0.75 | 0.5% |
| Magnesium stearate | 0.75 | 0.5% | 0.75 | 0.5% |
| Total | 150 | 100% | 150 | 100% |

Data from various further in vitro studies indicated that low viscosity HPMC (19-24% methoxyl, 7-12% hydroxypropyl, apparent viscosity of 2% aqueous solution at 20° C. around 3000 mPa·s) could be used as the sole release-controlling polymer while giving the desired release profile. Sticking was avoided using 1% magnesium stearate. Thus, final batches for clinical studies were prepared with the following compositions (masses in mg) and release profiles:

| Component | Mass | % wt | Mass | % wt | Mass | % wt |
|---|---|---|---|---|---|---|
| Bexagliflozin | 10 | 6.67% | 15 | 10% | 20 | 13.33% |
| HPMC (low viscosity) | 37.5 | 25% | 40 | 26.67% | 40 | 26.67% |
| Lactose monohydrate | 86 | 57.33% | 77.75 | 51.83% | 72.75 | 48.5% |
| Sodium bicarbonate | 15 | 10% | 15 | 10% | 15 | 10% |

-continued

| Component | Mass | % wt | Mass | % wt | Mass | % wt |
|---|---|---|---|---|---|---|
| Colloidal silicon dioxide | — | — | 0.75 | 0.5% | 0.75 | 0.5% |
| Magnesium stearate | 1.5 | 1% | 1.5 | 1% | 1.5 | 1% |
| Total | 150 | 100% | 150 | 100% | 150 | 100% |
| Release: 1 hour | 15% | | 13% | | 12% | |
| after 6 hours | 55% | | 53% | | 50% | |
| 12 hours | 90% | | 87% | | 85% | |

These three tablets were made by mixing the lactose monohydrate and bexagliflozin, then adding HPMC, sodium bicarbonate and silicon dioxide, and finally magnesium stearate. This mixture was tableted by direct compression with a 7 mm punch. The tablets were stable for 1 month at 40° C., 75% relative humidity.

These three extended release (XR) tablets were tested in human clinical trials to evaluate pharmacokinetics and pharmacodynamics, along with a 20 mg immediate release (IR) tablet. Tablets were administered once-daily for 5 days under fasted (days 1 & 2) or fed (day 3) conditions. Mean PK parameters±SD derived from the trials in the fasted condition were:

| | 20 mg IR | 10 mg XR | 15 mg XR | 20 mg XR |
|---|---|---|---|---|
| $C_{max}$ (ng/mL) | 238 ± 85.1 | 54.6 ± 22.9 | 75.9 ± 23.1 | 99.9 ± 77.9 |
| $T_{max}$ (h) | 1.0 | 3.0 | 5.0 | 4.0 |
| $AUC_{0\text{-}24\,h}$ (ng h $mL^{-1}$) | 961 ± 252 | 341 ± 123 | 525 ± 169 | 632 ± 334 |
| $AUC_{0\text{-}\infty}$ (ng h $mL^{-1}$) | 1024 ± 263 | 391 ± 133 | 615 ± 170 | 746 ± 321 |
| $t_{1/2z}$ (h) | 7.14 ± 3.88 | 8.15 ± 2.30 | 8.17 ± 2.85 | 9.42 ± 3.45 |

Thus, compared to the 20 mg immediate release tablet, the 20 mg extended release tablet's $C_{max}$ was about 40% and it showed a longer half-life, but with an apparent reduction of bioavailability of around 30%. Absorption and clearance were consistent across the three extended release doses, and $C_{max}$ and AUC values increased with increasing dose.

For the 20 mg IR formulation, food decreased the amount of and delayed the absorption of bexagliflozin, as demonstrated by lower $C_{max}$ and longer $T_{max}$. Although food decreased the rate of absorption of the 20 mg IR formulation, it had little impact on the overall bioavailability.

For the 10 mg XR formulation, food appeared to have little impact on the PK profile except for shortening of mean $T_{max}$. However, examination of the PK parameters revealed that the median $T_{max}$ values were the same under both fed and fasted conditions.

For the 15 mg and 20 mg XR formulations, food reduced $T_{max}$ but mean $C_{max}$ and $AUC_{0\text{-}\infty}$ were similar under fed and fasted conditions for both dose levels. These observations indicate that food may have accelerated but did not increase the magnitude of absorption of bexagliflozin following administration of the 15 mg and 20 mg XR formulations.

In terms of pharmacodynamics, all tablets were associated with significant dose-dependent glucosuria in healthy subjects. Glucose excretion occurred later with the XR formulations compared to the IR formulation, but the total daily glucose excretion was comparable. In general, urinary glucose excretion was highest in the first 12 hours post-dose and on day 2 under fasted and fed conditions for all tablets. Food appeared to have minimal effects on glucose excretion over 24 hours for all tablets as excretion under the fed state fell within ranges observed during the fasted conditions.

Although these XR formulations succeeded in reducing $C_{max}$ of bexagliflozin, the bioavailability and pharmacokinetics were more variable than desired. In particular, the $T_{max}$ was unacceptably variable, perhaps because of a failure to retain the tablet in the stomach. Early exit from the stomach could also explain the sporadic lower bioavailability, due in part to negation of the disruptive stresses which arise from acid-driven effervescence. Thus, further XR formulations were developed in order to reduce this variability.

Example 2—Pellet-Releasing Capsules

A capsule which disperses into many small pellets or granules in the stomach would reduce the chances that the total dose of bexagliflozin would be expelled from the stomach in a single event. Two approaches were thus proposed, both relying on capsules which release multiple bexagliflozin pellets. The first releases low density pellets which float in gastric acid; the second releases coated pellets.

Five formulations with floating pellets ('floater' capsules) were prepared and assessed as before by in vitro dissolution tests in 0.1 N HCl. The contents of these capsules were as follows (mg per capsule), along with the % of bexagliflozin which had been released after 12 hours:

| | A | B | C | D | E |
|---|---|---|---|---|---|
| Bexagliflozin | 15 | 15 | 15 | 15 | 15 |
| Glyceryl dibehenate | 150 | 25 | 87.5 | — | — |
| Cetostearyl alcohol | — | — | — | 150 | — |
| Stearic acid 50 | — | — | — | — | 150 |
| Eudragit RS PO* | 90 | 180 | 135 | 90 | 90 |
| Eudragit RS 30D* | — | 50 | 25 | — | — |
| Triethyl citrate (TEC) | — | 10 | 10 | — | — |
| Microcrystalline cellulose (MCC) | 75 | 50 | 67.5 | 75 | 75 |
| Polyvinylpolypyrrolidone (PVPP) | 30 | 40 | 30 | 30 | 30 |
| Total | | | 360 mg | | |
| Dissolution % (12 hours) | 89.8 | 68.9 | 79.4 | 88.4 | 90.2 |

*Poly(ethyl acrylate-co-methyl methacrylate-co-trimethylammonioethyl methacrylate chloride) 1:2:0.1

Twenty-one formulations with coated pellets were tested, with seven types of pellet each with three different coatings. Compositions and 12 hour dissolution 0% were as follows:

| | A | | | B | | | C |
|---|---|---|---|---|---|---|---|
| | Core pellet | | | | | | |
| Bexagliflozin | | 15 | | | 15 | | 15 |
| MCC | | 170 | | | 170 | | 170 |
| PVPP | | 15 | | | 15 | | 15 |
| Poloxamer 188 | | — | | | — | | — |
| XR coating | 1 | 2 | 3 | 1 | 2 | 3 | 1 |
| Eudragit RS 30D | 6 | 14 | 18 | 3 | 5 | 7 | — |
| Eudragit RL 30D* | 6 | 14 | 13 | 9 | 15 | 21 | 12 |
| Lactose | — | — | — | — | — | — | — |
| TEC | 2.4 | 5.6 | 7.2 | 2.4 | 4.0 | 5.6 | 2.4 |
| Talc | 6 | 14 | 18 | 6 | 10 | 14 | 6 |
| Total | 220.4 | 247.6 | 261.2 | 220.4 | 234.0 | 247.6 | 220.4 |
| Dissolution % | 71.2 | 56.2 | 53.4 | 75.4 | 69.8 | 65.9 | 81.4 |

| | C | | D | | | E | |
|---|---|---|---|---|---|---|---|
| | Core pellet | | | | | | |
| Bexagliflozin | 15 | | | 15 | | 15 | |
| MCC | 170 | | | 170 | | 155 | |
| PVPP | 15 | | | 15 | | 15 | |
| Poloxamer 188 | — | | | — | | 45 | |
| XR coating | 2 | 3 | 1 | 2 | 3 | 1 | 2 |
| Eudragit RS 30D | — | — | — | — | — | — | — |
| Eudragit RL 30D | 16 | 24 | 12 | 16 | 24 | 13.8 | 18.4 |
| Lactose | — | — | 1.2 | 1.6 | 2.4 | — | — |
| TEC | 3.2 | 4.8 | 2.4 | 3.2 | 4.8 | 2.8 | 3.7 |
| Talc | 8 | 12 | 6 | 8 | 12 | 6.9 | 9.2 |
| Total | 227.2 | 240.8 | 221.6 | 228.8 | 243.2 | 253.5 | 261.3 |
| Dissolution % | 77.4 | 75.7 | 84.1 | 74.9 | 79.2 | 98.3 | 90.5 |

| | E | F | | | G | | |
|---|---|---|---|---|---|---|---|
| | Core pellet | | | | | | |
| Bexagliflozin | 15 | | 15 | | | 15 | |
| MCC | 155 | | 155 | | | 225 | |
| PVPP | 15 | | 15 | | | 15 | |
| Poloxamer 188 | 45 | | 45 | | | 45 | |
| XR coating | 3 | 1 | 2 | 3 | 1 | 2 | 3 |
| Eudragit RS 30D | — | 23.0 | 32.2 | 31.4 | 27.0 | 31.5 | 36.0 |
| Eudragit RL 30D | — | — | — | — | — | — | — |
| Lactose | — | — | — | — | — | — | — |
| TEC | 5.5 | 4.6 | 6.4 | 8.3 | 7.2 | 8.4 | 9.6 |
| Talc | 13.8 | 11.5 | 16.1 | 20.7 | 18.0 | 21.0 | 24.0 |
| Total | 276.9 | 269.1 | 284.7 | 300.4 | 361.2 | 371.4 | 381.6 |
| Dissolution % | 99.0 | 50.5 | 27.2 | 27.3 | 50.5 | 27.2 | 27.3 |

*Poly(ethyl acrylate-co-methyl methacrylate-co-trimethylammonioethyl methacrylate chloride) 1:2:0.2

Based on the in vitro dissolution tests, formulations were chosen as follows:

| | Floater A | | Coated G | |
|---|---|---|---|---|
| | mg per capsule | % wt | mg per capsule | % wt |
| Bexagliflozin | 15 | 4.2 | 15 | 3.9 |
| Glyceryl dibehenate | 150 | 41.7 | — | — |

-continued

| | Floater A | | Coated G | |
|---|---|---|---|---|
| | mg per capsule | % wt | mg per capsule | % wt |
| Eudragit RS PO | 90 | 25.0 | — | — |
| Microcrystalline cellulose | 75 | 20.8 | 225 | 58.6 |

-continued

| | Floater A | | Coated G | |
|---|---|---|---|---|
| | mg per capsule | % wt | mg per capsule | % wt |
| Polyvinylpolypyrrolidone | 30 | 8.3 | 15 | 3.9 |
| Poloxamer 188 | — | — | 45 | 11.7 |
| Pellet core weight | 360 | 100% | 300 | |
| Eudragit RS 30D | — | — | 36 | 9.4% |
| Eudragit RL 30D | — | — | 13.4 | 3.5% |
| Triethyl citrate | — | — | 9.9 | 2.6% |
| Talc | — | — | 24.7 | 6.4% |
| Total pellet weight | 360 | 100% | 384 | 100% |
| Capsule | | 0#, green | | |

To make the pellets: bexagliflozin, glyceryl dibehenate (retardant and floating agent), ethyl acrylate/methyl methacrylate copolymer (Eudragit RS PO; matrix material), microcrystalline cellulose (MCC; filler) and polyvinylpolypyrrolidone (binder and disintegrant) were mixed; and then water was added to provide wet granules. Extrusion and spheronisation gave wet pellets, which were then dried to give the floating pellets, which were then filled into capsules.

To make the coated granules bexagliflozin, microcrystalline cellulose (filler), poloxamer 188 (solubilizer) and polyvinylpolypyrrolidone (binder and disintegrant) were mixed, and then water was added to provide wet granules. Extrusion and spheronisation gave wet pellets which were then dried. A coating composition was then formed by mixing talc (lubricant), TEC (plasticizer) and water to give a suspension which was then mixed with the two Eudragit copolymner components (extended release coatings). This was used to coat the dry pellets and the coated pellets were filled into capsules.

Accelerated stability studies showed that the compositions were stable for 8 weeks at 40° C. with 750% RH, but their dissolution profiles changed significantly (slower for the coated pellets, faster for the floaters). Thus, these formulations succeed in altering the pharmacokinetic profile of bexagliflozin, but their shelf-life is not optimal for commercial purposes.

Example 3—Floating Tablets

A tablet which floats in gastric contents could delay transit from the stomach and thus avoid rapid premature expulsion from the stomach as discussed in Example 1 above.

Two prototype formulations were prepared, with compositions as follows (mg per tablet):

| | H | I |
|---|---|---|
| Bexagliflozin | 15 | 15 |
| Nonionic polyethylene oxide | 105 | 60 |
| Glyceryl dibehenate | 100 | 120 |
| Lactose (filler) | — | 25 |
| Microcrystalline cellulose (MCC) (filler) | 77 | 77 |
| Colloidal silicon dioxide | 1.5 | 1.5 |
| Magnesium stearate | 1.5 | 1.5 |
| Total | 300 | 300 |

These tablets were compressed to a hardness of 40 N or 50 N and then subjected to in vitro dissolution tests as in Examples 1 & 2. The percentage of bexagliflozin released at 8 and 12 hours was as follows:

| | H, 40 N | H, 50 N | I, 40 N | I, 50 N |
|---|---|---|---|---|
| 8 hours | 59.8 | 67.9 | 82.7 | 51.4 |
| 12 hours | 95.6 | 95.2 | 100 | 76.9 |

Based on these results the final tablet formulation was selected as follows:

| | mg per tablet | % wt | Function |
|---|---|---|---|
| Bexagliflozin | 15 | 5 | Active ingredient |
| Polyethylene oxide (PEO) | 105 | 35 | Mucoadhesive matrix |
| Glyceryl dibehenate | 100 | 33.3 | Retardant and floating agent |
| Microcrystalline cellulose | 77 | 25.7 | Filler |
| Colloidal silicon dioxide | 1.5 | 0.5 | Glidant |
| Magnesium stearate | 1.5 | 0.5 | Lubricant |
| Total | 300 | 100% | |

These tablets are made by (a) combining bexagliflozin, MCC, gyceryl dibehenate and PE and (b) combining the silicon dioxide and magnesium stearate, and then combining (a) & (b) for direct compression to form tablets.

Accelerated stability studies showed that the tablets were stable for 8 weeks at 40° C. with 750 RH, with minimal differences in dissolution profile.

Example 4—Tablets with More Rapid Extended Release

Further work was performed to obtain faster release from the mucoadhesive tablets of Example 3 (aiming for complete release with 4-6 hours), while maintaining a similar tablet composition and the direct compression manufacturing technique. Thus, the tablet composition was modified and investigations led to two further formulations:

| | J (mg) | J (% wt) | K (mg) | K (% wt) |
|---|---|---|---|---|
| Bexagliflozin | 15 | 4.3 | 15 | 4.3 |
| Polyethylene oxide | 65 | 18.8 | 50 | 14.3 |
| Glyceryl dibehenate | 120 | 34.7 | 120 | 34.4 |
| Lactose | 45 | 13.0 | — | — |
| Poloxamer 188 | 42 | 12.1 | 87 | 24.9 |
| Microcrystalline cellulose (MCC) | 50 | 14.5 | 50 | 14.3 |
| Polyvinylpolypyrrolidone | — | — | 15 | 4.3 |
| Colloidal silicon dioxide | 4.5 | 1.3 | 6 | 1.7 |
| Magnesium stearate | 4.5 | 1.3 | 6 | 1.7 |
| Total | 346 mg | 100% | 349 mg | 100% |

These tablets were manufactured in the same manner as Example 3 i.e. all components except the lubricant and glidant are combined, and then these are mixed with the combined lubricant/glidant and pressed into tablets by direct compression to a hardness of 30 N.

The tablets' dissolution profiles over 8 hours were as follows:

| Hours | 0 | 1 | 2 | 3 | 4 | 5 | 6 | 8 |
|---|---|---|---|---|---|---|---|---|
| J % | 0.0 | 10.7 | 23.6 | 38.3 | 59.5 | 85.7 | 94.7 | 94.2 |
| K % | 0.0 | 7.4 | 20.8 | 46.8 | 83.9 | 95.4 | 94.2 | 92.0 |

The tablets were stable at 40° C. at 75% RH for at least 8 weeks. After this storage tablet J's dissolution profile showed negligible differences, but tablet K's release profile was slightly faster. Furthermore, both tablets became slightly harder after storage.

Thus, faster release than in Example 3 was successfully achieved.

Example 5—Lactose-Free Extended Release Tablets

Tablet J from Example 4 includes lactose. As this is an animal-derived material, alternative fillers were tested aiming at tablets having a similar release profile. In particular, mannitol, sorbitol, xylitol and maltodextrin were tested as alternatives (45 mg in each case).

All four of these ingredients were first shown to be compatible with bexagliflozin.

Using mannitol in place of lactose gave tablets with a similar release behaviour, with both formulations reaching >90% released in 5 hours in vitro. Higher tablet hardness was tried (45-55N), which resulted in a shorter floating time and thus slightly faster dissolution.

Maltodextrin, sorbitol and xylitol resulted in slightly faster release profiles than lactose and mannitol, possibly due to their higher solubility.

Overall, it was feasible to achieve comparable dissolution behavior by replacing lactose with alternative excipients.

Example 6—Extended Release Tablets for Clinical Trials

Five floating mucoadhesive tablets were prepared for clinical testing, including the final formulation from Example 3 and tablets J & K from Example 4. Their compositions and properties were:

| | L | M | N | O | P |
|---|---|---|---|---|---|
| Bexagliflozin | 15 | 15 | 15 | 15 | 15 |
| Polyethylene oxide | 105 | 85 | 65 | 65 | 50 |
| Glyceryl dibehenate | 100 | 100 | 120 | 120 | 120 |
| Lactose anhydrous | — | 45 | 45 | 45 | — |
| Poloxamer 188, micronized | — | — | 42 | 42 | 87 |
| MCC | 77 | 77 | 50 | 50 | 50 |
| PVPP | — | — | — | — | 15 |
| Colloidal silicon dioxide | 1.5 | 1.5 | 1.5 | 4.5 | 6 |
| Magnesium stearate | 1.5 | 1.5 | 1.5 | 4.5 | 6 |
| Total | 300 | 325 | 340 | 346 | 349 |
| Hardness range | 40 N | 40-50 N | 20-30 N | 30 N | 30 N |

In general, these were manufactured by combining (a) a mixture of bexagliflozin and MCC (b) a mixture of the lubricant and glidant (c) a mixture of the remaining ingredients. This mixture was then compressed to a desired hardness using a rotary compression machine with a 14×6 mm caplet shaped punch. Friability was no more than 1% w/w.

Some sticking was seen using formulation N and so the amount of magnesium stearate was increased to 4.5 mg and this resolved the issue. A further increase in the amount of silicon dioxide then provided formulation O.

Formulations L, M and O were found to have the best overall properties in dissolution, stability, etc. These three tablets were selected for further study of the impact of dissolution times: tablet L transitioned from 80% to 90% release between the 10 and 12 hour samples; for tablet M this occurred between 8 and 10 hours; and for tablet O it occurred between 5 and 6 hours. Thus, these tablets were named XR11, XR8 and XR5 to reflect their dissolution profiles, and they were taken forwards to clinical trial testing.

Example 7—Alternative Doses in Tablets for Clinical Trials

Based on the XR5 results in Example 6 (tablet 0) further floating mucoadhesive tablets were prepared in the same way, but containing 10 mg or 30 mg bexagliflozin. Additionally, these tablets had a film coating made from Opdary II white. The final tablets had the following compositions (mg per tablet):

| | Q10 | Q15 | Q30 |
|---|---|---|---|
| Bexagliflozin | 10 | 15 | 30 |
| Polyethylene oxide | 65 | 65 | 65 |
| Glyceryl dibehenate | 120 | 120 | 120 |
| Lactose anhydrous | 45 | 45 | 45 |
| Poloxamer 188, micronized | 42 | 42 | 42 |
| MCC | 50 | 50 | 50 |
| Colloidal silicon dioxide | 4.5 | 4.5 | 4.5 |
| Magnesium stearate | 4.5 | 4.5 | 4.5 |
| Total | 341 | 346 | 361 |
| Hardness range | 30-40 N | 30-40 N | 30-40 N |
| Coating (Opadry II white) | 10.23 | 10.38 | 10.83 |
| Coated tablet weight | 351.23 | 356.38 | 371.83 |
| Friability | | ≤1% by weight | |

Coated tablets were cured for up to 24 hours at 50° C. to study the effect on hardness. The tablets' dissolution release profile and hardness were not affected by curing and so this treatment was not used in further studies.

Accelerated stability studies showed no effect on dissolution properties for the tablets.

Release of bexagliflozin in in vitro dissolution tests (performed as above) were as follows:

| Time (hours) | Q10 | Q15 | Q30 |
|---|---|---|---|
| 1 | 9% | 9% | 8% |
| 3 | 47% | 44% | 44% |
| 5 | 85% | 82% | 80% |
| 8 | 96% | 96% | 94% |

The stability and release profiles of these tablets were in accordance with the intended properties and so they were taken forwards into human clinical testing, along with the XR5, XR8 and XR11 tablets from Example 6.

Example 8—Particle Size Distribution

The effect of crystalline bexagliflozin particle size distribution on tablet dissolution in an in vitro dissolution test was assessed in XR5-type tablets having 20 mg or 30 mg total bexagliflozin dose. Various particle size distributions were tested, with d(0.9) values ranging from about 10 μm up to around 700 μm (i.e. particle size distributions in which 90% of the cumulative volume of the crystalline bexagliflozin particles had a diameter no more than 10 μm up to 700 μm) e.g. with d(0.9) of 220 μm or 325 μm. No significant variations in tablet dissolution profile were observed with these different d(0.9) values, so particle size distribution of crystalline bexagliflozin is not seen as an important parameter for tablet dissolution.

Example 9—Clinical Trials

A 2-part Phase 1 open-labeled study was conducted to assess the pharmacokinetics of multiple oral doses of these floating tablets in healthy male subjects. Part 1 assessed the PK profiles in XR5, XR8 or XR11 tablets (Example 6). Part 2 assessed three dosage strengths (10 mg, 15 mg, and 30 mg) of tablets with a 5-hour release profile (Example 7). Secondary objectives were to assess the safety and tolerability of bexagliflozin and to evaluate the effect of food on PK parameters.

Part 1 used a crossover design. 20 subjects were dosed with each of the three 15 mg tablets, or with a 20 mg capsule (size 2 white opaque gelatin capsules containing 20 mg bexagliflozin, and microcrystalline cellulose, silicified). There were 4 dosing periods with no washout in between. The first dosing period consisted of 2 days of once-daily dosing in the fasted state, followed by 1 day of dosing in the fed state. The second to fourth dosing periods consisted of 1 day of dosing in the fasted state and 1 day of dosing in the fed state. Subjects were randomized to receive 1 of the 4 formulations in 1 of the 24 permutations possible for a 4-period crossover study with a single constraint that the first dosing period incorporated each formulation 5 times.

Part 2 used a parallel design in 30 subjects. Tablets were administered once daily for 2 days in the fasted state and for 1 day in the fed state.

Tablets (or capsules) were administered with approximately 200 mL of water, while subjects were in an upright position, to be swallowed without chewing. Dosing while fasting occurred following a minimum of a 10-hour overnight fast. For doses in the fasted state, breakfast was provided 1 hour after dosing. Dosing in the fed state occurred 30 minutes after the start of a standard meal. Bexagliflozin plasma concentrations were determined by a validated HPLC MS/MS method from samples of whole venous blood anticoagulated with $K_2$EDTA (see below).

FIG. 1 shows the geometric mean plasma concentration of bexagliflozin in fasted subjects in part 1 of the trial. The capsule shows a high $C_{max}$, but this was successfully decreased using the XR5, XR8 or XR11 tablets, providing an extended absorption phase with a median $T_{max}$ of 3 hours for all three XR tablets in fasted subjects (compared to 1 hour with the capsules). Taking account of their lower dose (15 mg vs. 20 mg), the normalized $C_{max}$ of the tablets was reduced to <5 ng/mL/mg compared to 10.2 ng/mL/mg. $C_{max}$ was also reduced in the fed state, although to a lesser extent; XR11 gave the greatest decrease. After reaching $C_{max}$, plasma concentrations decreased in a biphasic manner for the tablets and also for the capsules. Overall, specific pharmacokinetic parameters were as follows:

| | XR11 | | XR8 | | XR5 | | Capsule | |
|---|---|---|---|---|---|---|---|---|
| | Fasted | Fed | Fasted | Fed | Fasted | Fed | Fasted | Fed |
| $C_{max}$ (ng/mL) | 44.2 | 85.0 | 48.5 | 95.6 | 68.9 | 118 | 204 | 174 |
| $AUC_{0-24}$ (ng h $mL^{-1}$) | 409 | 609 | 497 | 633 | 562 | 723 | 1019 | 1025 |
| $AUC_{0-t}$ (ng h $mL^{-1}$) | 410 | 600 | 467 | 634 | 562 | 720 | 1018 | 1023 |
| $AUC_{0-\infty}$ (ng h $mL^{-1}$) | 497 | 720 | 628 | 741 | 700 | 822 | 1111 | 1118 |
| $T_{max}$ (h) | 3.0 | 5.0 | 3.0 | 5.0 | 3.0 | 5.0 | 1.0 | 3.0 |

Figure 2:
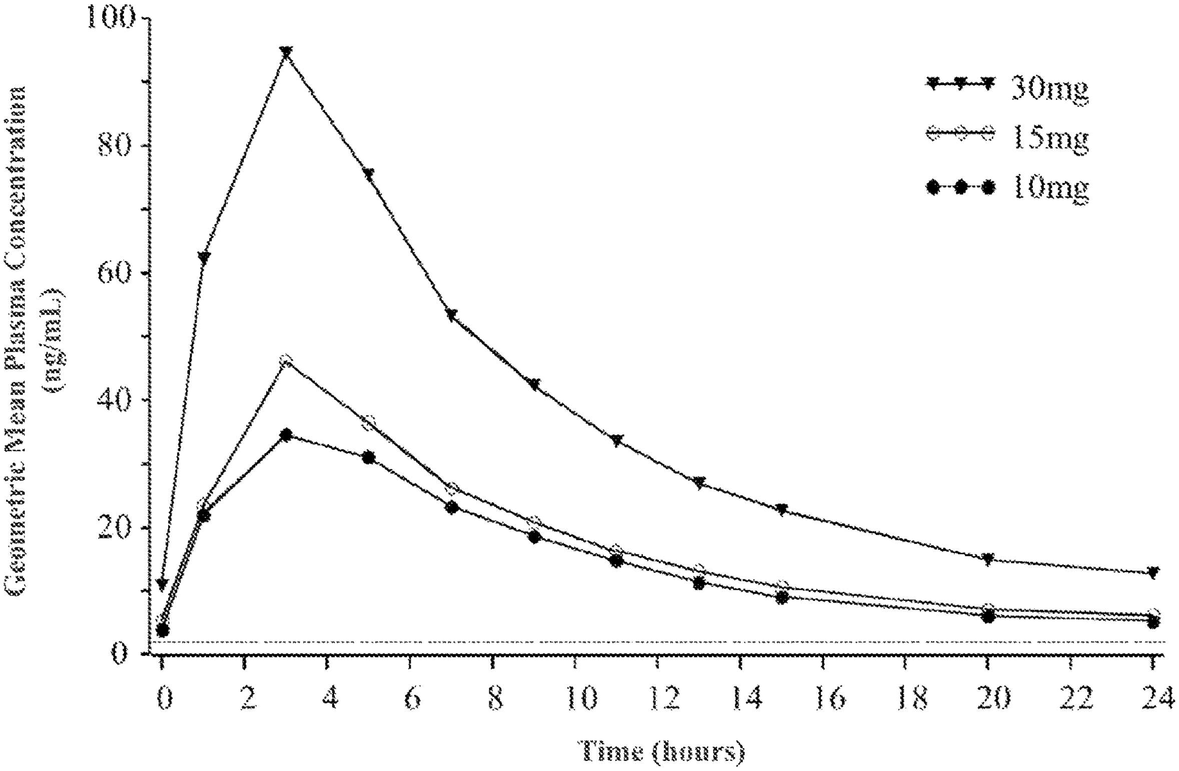
FIG. 2 shows the geometric mean plasma concentration (ng/mL) of bexagliflozin in fasted subjects who received 10 mg (●), 15 mg (○), or 30 mg (▼) tablets.

FIG. 2 shows the geometric mean plasma concentration of bexagliflozin in fasted subjects in part 2 of the trial. All three doses (10, 15, and 30 mg) showed an extended absorption phase with a median $T_{max}$ of 3 hours for all doses in fasted subjects. After reaching $C_{max}$, plasma concentrations decreased in a biphasic maimer for all three tablets. Exposure ($AUC_{0-24\ h}$ and $C_{max}$) generally appeared to increase in a dose-proportional manner for the 10-30 mg range, but clearance and volume of distribution were dose-independent. Overall, specific pharmacokinetic parameters were as follows:

| | Q10 | | Q15 | | Q30 | |
|---|---|---|---|---|---|---|
| | Fasted | Fed | Fasted | Fed | Fasted | Fed |
| $C_{max}$ (ng/mL) | 41.0 | 85.9 | 56.7 | 106 | 102 | 236 |
| $AUC_{0-24}$ (ng h $mL^{-1}$) | 411 | 523 | 445 | 704 | 1090 | 1461 |
| $AUC_{0-t}$ (ng h $mL^{-1}$) | 386 | 523 | 455 | 704 | 939 | 1461 |
| $AUC_{0-\infty}$ (ng h $mL^{-1}$) | 465 | 606 | 583 | 783 | 1246 | 1572 |
| $T_{max}$ (h) | 3.0 | 3.0 | 3.0 | 5.0 | 3.0 | 5.0 |

In summary of the pharmacokinetic study, administration of XR11, XR8, and XR5 tablets resulted in a prolonged absorption relative to the capsule formulation. Mean exposure was higher following administration of 20 mg of the capsule formulation than 15 mg of the XR formulations following administration in either dietary state. Among the XR formulations XR5 produced the greatest exposure. Administration of the XR formulations in the fed state resulted in an increase in exposure of 27% to 49% and 71% to 97%, for $AUC_{0-24}$ and $C_{max}$, respectively, compared to administration in the fasted state. Administration of 10, 15, and 30 mg of the XR5 formulation resulted in a dose proportional increase in exposure.

Analytical Methods for Human Plasma Samples

As noted above, bexagliflozin concentrations have been determined in human plasma samples by a validated HPLC MS/MS method. One example of a suitable method is provided as follows.

The internal standard 'IS' was bexagliflozin in which the 6 hexose carbons are substituted with $^{13}C$. Other internal standards, for example tolbutamide, can be used, but an isotopically labeled internal standard is preferred.

For each run, a “Blank+IS” and a “Blank+Drug” sample are included to monitor any contribution from the IS to the analyte or vice versa. The solvent for all standards and reconstitution is methanol. The matrix is human plasma anticoagulated with $K_2$EDTA.

The analytical method proceeds as follows: thaw standards, QCs, blank matrix and study samples (as applicable) and vortex for ≈3 minutes before pipetting; add 100 μL of blank plasma into Blank, Blank+IS, Blank+Drug, Test, and Calibration Standards; spike Blank+Drug with 5 μL of 16000 ng/mL bexagliflozin spiking solution; spike Test with 5 μL of 80 ng/mL spiking solution; to Calibration Standards, add 5 μL of spiking solutions at each concentration; to QC tubes, add 100 μL of QC samples at the appropriate concentrations and number of replicates; if applicable, add 100 μL of each Study Sample to the appropriate tubes; add 5 μL of MeOH into Blank, Blank+IS, QCs and Study Samples tubes, as applicable; add 50 μL of IS into Test, Blank+IS, Calibration Standard, and QC (and Study Sample, if applicable) tubes; add 50 μL of MeOH into Blank and Blank+Drug tubes; vortex for approximately 2 minutes at high speed.

The protein precipitation extraction procedure is as follows: add 500 μL acetonitrile (ACN) into all tubes; vortex tubes for approximately 3 minutes at high speed, then centrifuge for 10 minutes at 3000 rpm; transfer the supernatant into 16×100 mm labeled tubes; evaporate to dryness in a 40° C. bath under nitrogen stream for ≈10 minutes; reconstitute all samples with 200 μL of MeOH to each tube and vortex for ≈1 minute at high speed; transfer to autosampler vials for LC-MS/MS analysis; centrifuge vials for ≈5 minutes at 3000 rpm.

Equipment used was: Vacuum Degasser, DGU 14A, Shimadzu Corp.; Solvent Delivery System, LC-10ADvp, SCL-10Avp, Shimadzu Corp.; Autoinjector, HTC PAL, CTC Analytics; Column Heater at 35° C., TS-130, PHENOMENEX™; Mass Spectrometer, Triple Quadrupole MS (API 4000), Sciex.

| Human Plasma Analytical Method | | | | | | |
|---|---|---|---|---|---|---|
| Analyte | Bexagliflozin | | | | | |
| Matrix | $K_2$ EDTA Human Plasma | | | | | |
| Calibration Standard concentrations | 1, 2, 8, 48, 150, 500, 800, and 1000 ng/mL | | | | | |
| Quality Control concentrations | 1, 3, 80, and 800 ng/mL | | | | | |
| Internal Standard | [$^{13}$C]-bexagliflozin at 500 ng/mL | | | | | |
| Regression type | Linear analysis with $1/x^2$ weighting | | | | | |
| Sample volume | 100 μL | | | | | |
| Extraction procedure summary | Protein precipitation extraction of the analyte and internal standard from $K_2$EDTA human plasma using acetonitrile (ACN) | | | | | |
| Reconstitution solvent | 200 μL of ACN:$H_2O$:1M $NH_4OAc$/25:75:0.5 (v:v:v) | | | | | |
| Chromatography Settings | | | | | | |
| Column type | Synergi Hydro-RP, 80 A, 50 × 2.00 mm, 4 μm, Phenomenex | | | | | |
| Column switching | 1.1-2.5 min to mass spec | | | | | |
| Mobile phase composition | A: Water: 1M $NH_4OAc$:HCOOH/1000:0.5:1 (V:V:V)<br>B: ACN:HCOOH/1000:1 (V:V) | | | | | |
| Program | Gradient | | | | | |
| Time (min) | 0.5 | 2.0 | 2.2 | 4.2 | 4.3 | 5.3 |
| % B | 30 | 70 | 95 | 95 | 30 | Stop |
| Flow Rate (mL/min) | 0.4 | 0.4 | 0.4 | 0.4 | 0.4 | — |
| Autoinjector temperature | 10° C. | | | | | |
| Autoinjector wash solvent 1 | ACN:HCOOH/100:2 (V:V) | | | | | |
| Autoinjector wash solvent 2 | MeOH:$H_2O$:HCOOH/30:70:2 (V:V:V) | | | | | |
| Flow rate | ≈400 μL/min | | | | | |
| Analysis time | ≈5.8 min | | | | | |
| Injection volume | 10 μL | | | | | |
| Retention time | bexagliflozin ≈ 1.80 min<br>[$^{13}$C]-bexagliflozin ≈ 1.80 min | | | | | |

| Mass Spectrometer Settings (Recommended Values) | |
|---|---|
| Source Temperature (TEM): | 500° C. |
| Collision Gas (CAD): | 12 psig $N_2$ (82737 Pa) |
| Curtain Gas (CUR): | 20 psig $N_2$ (137895 Pa) |
| Ion Source Gas 1 (GS1): | 70 psig $N_2$ (482633 Pa) |
| Ion Source Gas 2 (GS2): | 50 psig $N_2$ (344737 Pa) |
| Ion Spray Voltage (IS): | 5500 V |
| Entrance Potential (EP): | 10 V |
| Scan duration: | 3.5 min |

-continued

| Compound | Ionization Mode | Dwell Time (msec) | Declustering Potential (V) | Collision Energy (eV) | Collision Exit Potential (V) | Transition (m/z) |
|---|---|---|---|---|---|---|
| bexagliflozin | TIS+ | 200 | 50 | 37 | 14 | 482.2 → 167.3 |
| [$^{13}$C]-bexagliflozin (IS) | TIS+ | 200 | 80 | 36 | 30 | 488.2 → 168.9 |

Example 10 μAdditional Tablet Strengths

To supplement Example 9, tablets of 3 and 90 mg bexagliflozin were prepared. The 3 mg tablets were similar to the tablets of Example 9, but excipients were removed from the 90 mg tablets and these lost their floating characteristics. Placebo tablets were also prepared to observe floating properties. Mucoadhesive was retained in all tablets. The new tablets had these compositions:

| | R | S | Placebo |
|---|---|---|---|
| Bexagliflozin | 3 | 90 | — |
| Polyethylene oxide | 65 | 65 | 65 |
| Glyceryl dibehenate | 120 | 120 | 120 |
| Lactose anhydrous | 45 | 45 | 45 |
| Poloxamer 188, micronized | 42 | 42 | 42 |
| MCC | 50 | — | 70 |
| Colloidal silicon dioxide | 4.5 | 4.5 | 4.5 |
| Magnesium stearate | 4.5 | 4.5 | 4.5 |
| Total | 334 | 371 | 361 |
| Hardness range | 30-40N | 30-40N | 30-40N |
| Coating (Opadry II white) | 10.02 | 11.13 | 10.83 |
| Coated tablet weight | 344.02 | 382.13 | 371.83 |
| Friability | | <1.0% w/w | |

The absence of MCC in tablet S was found to affect compressibility, with severe lamination observed. Thus, further 90 mg tablets with 25 or 50 mg MCC were prepared, or with a combination of 20 mg lactose and 25 mg MCC. Furthermore, the lubricant and glidant were co-sifted with the bexagliflozin to reduce lamination. Based on observed dissolution and floating profiles the following tablets were prepared for clinical use:

| | T3 | T10 | T30 | T90 |
|---|---|---|---|---|
| Bexagliflozin | 3 | 10 | 30 | 90 |
| Polyethylene oxide | 65 | 65 | 65 | 65 |
| Glyceryl dibehenate | 120 | 120 | 120 | 120 |
| Lactose anhydrous | 45 | 45 | 45 | — |
| Poloxamer 188, micronized | 42 | 42 | 42 | 42 |
| MCC | 50 | 50 | 50 | 50 |
| Colloidal silicon dioxide | 4.5 | 4.5 | 4.5 | 4.5 |
| Magnesium stearate | 4.5 | 4.5 | 4.5 | 4.5 |
| Total | 334 | 341 | 361 | 376 |
| Hardness range | 30-40N | 30-40N | 30-40N | >50N |
| Coating (Opadry II white) | 10.02 | 10.23 | 10.83 | 11.28 |
| Coated tablet weight | 344.02 | 352.13 | 371.83 | 387.28 |
| Friability | | <1.0% w/w | | |

These were made as before, by mixing (a) bexagliflozin plus MCC by co-sifting with (b) polyethylene oxide, poloxamer, lactose, and glyceryl dibehenate, followed by addition of a mixture of (c) magnesium stearate and silicon dioxide. This material was compressed to the desired hardness in a 14×6 mm caplet-shaped punch, and the tablets were then coated.

Release of bexagliflozin from these tablets was assessed by in vitro dissolution tests according to USP <711> as discussed above (USP Apparatus 1, charged with 900 mL of 0.1 N HCl, stirred at 50 rpm, 37° C., sampling without replacement). The following table presents appropriate chromatographic conditions for the detection of bexagliflozin in 0.1 N HCl. The 10 mL samples from Apparatus 1 are passed through a 10 μm PVDF filter and 50 μL injected onto the chromatography column.

| | |
|---|---|
| Column | Waters Sunfire $C_{18}$, 50 × 4.6 mm, 3.5 μm |
| Mobile Phase | 0.1% $H_3PO_4$ (aq.):Acetonitrile (59:41) Isocratic |
| Column temperature | 40° C. |
| Injection volume | 50 μL |
| Flow rate | 1.0 mL/minute |
| Detection wavelength | 225 nm |
| Auto sampler temperature | 20° C. |
| Run time | 6 minutes |
| Diluent | Methanol:Water (90:10 v/v) |
| Needle wash | Methanol |
| Bexagliflozin elution time | ≈2.26 minutes |

Results from these in vitro dissolution tests were as follows:

| Time (hours) | T3 | T10 | T30 | T90 |
|---|---|---|---|---|
| 1 | 8% | 8% | 6% | 5% |
| 3 | 35% | 31% | 29% | 24% |
| 5 | 62% | 57% | 51% | 44% |
| 8 | 90% | 84% | 78% | 72% |

Specific pharmacokinetic parameters for the T10 and T30 tablets in a clinical study in fed and fasted patients were as follows:

| | T10 | | T30 | |
|---|---|---|---|---|
| | Fasted | Fed | Fasted | Fed |
| $C_{max}$ (ng/mL) | 62.4 | 99.3 | 203 | 283 |
| $AUC_{0-t}$ (ng h mL$^{-1}$) | 437 | 517 | 1639 | 1656 |
| $AUC_{0-\infty}$ (ng h mL$^{-1}$) | 461 | 539 | 1733 | 1697 |
| $T_{max}$ (h) | 3.0 | 4.0 | 4.0 | 4.0 |

Example 11—Further Mucoadhesive Clinical Tablets

Based on the preceding examples, tablets were prepared for clinical studies as follows:

| | U5 | U10 | U20 | Placebo |
|---|---|---|---|---|
| Bexagliflozin | 5 | 10 | 20 | 0 |
| Polyethylene oxide | 65 | 65 | 65 | 65 |

-continued

| | U5 | U10 | U20 | Placebo |
|---|---|---|---|---|
| Glyceryl dibehenate | 120 | 120 | 120 | 120 |
| Lactose monohydrate | 45 | 45 | 45 | 45 |
| Poloxamer 188, micronized | 42 | 42 | 42 | 42 |
| MCC | 70 | 70 | 70 | 70 |
| Colloidal silicon dioxide | 4.5 | 4.5 | 4.5 | 4.5 |
| Magnesium stearate | 7.5 | 7.5 | 7.5 | 7.5 |
| Core total | 359 | 364 | 374 | 354 |
| Coating (Opadry II blue) | 10.77 | 10.92 | 11.22 | 10.62 |
| Coated tablet weight | 369.77 | 374.92 | 385.22 | 364.62 |
| Target hardness (up to 70N) | 45-55N | 45-55N | 45-55N | 45-55N |

The tablets were manufactured as follows: (i) co-sifting the bexagliflozin, colloidal silicon dioxide and 80% of the MCC using a vibrational sifter with a #20 sieve; (ii) blending the sifted material for 6 minutes in a container tumbler at 14 rpm (U5) or 18 rpm (U10 & U20); optionally (iii) sifting this material with the remaining MCC through a conical screen mill with a 813 μm screen at 1000 rpm, to give mixture 'A'; (iv) sifting the polyethylene oxide, glyceryl dibehenate and lactose using a vibrational sifter with a #20 sieve, to give mixture 'B'; (v) blending mixtures 'A' and 'B' in a container tumbler at 14 rpm; (vi) adding magnesium stearate which has been sifted through a #30 sieve and blending in a container tumbler at 14 rpm; (vii) compressing this material into tablet cores using 14.8×6.5 mm bevelled caplet-shaped punches and appropriate dies with a Korsch XL100 press, using 10 punch sets with 20-50 rpm force feeder and 55-70 rpm turret, or with a Killian T-300 press with 32 punch sets and a minimal force feeder; (viii) de-dusting; and (ix) coating using a 18% w/w suspension of the coating material in a 600 mm (U5) or 800 mm (U10 & U20) pan.

Release of bexagliflozin in in vitro dissolution tests were as follows, measured in a USP Apparatus 1 with 900 mL of 0.1 N HCl maintained at 37±0.5° C. and stirred at 50 rpm:

| Time (hours) | U5 | U10 | U20 |
|---|---|---|---|
| 1 | 10% | 9% | 6% |
| 3 | 40% | 34% | 27% |
| 5 | 66% | 58% | 48% |
| 8 | 93% | 88% | 80% |
| 10 | 95% | 96% | 94% |

The tablets were confirmed to be stable. The U20 tablet was selected for clinical uses requiring a 20 mg dose of bexagliflozin.

Further batches of tablets were prepared in a similar way, with minor variations. For instance, step (vii) was modified to use a Killian T-200 press with 19 heads. Furthermore, the concentration of coating material in step (ix) was reduced from 18% to 12%. Tablets made by these modified processes had the desired properties.

A reference batch of U20 tablets was prepared, and in vitro dissolution tests on a sample of tablets showed release of 7%, 27%, 50% and 86% of bexagliflozin after 1, 3, 5 and 8 hours, respectively. Tests were performed on nine further manufacturing batches (all tested at 1, 5 and 8 hours; five also tested at 3 hours) and $f_2$ values were within the range of 54 to 94 compared to the reference tablets.

Example 12—Stability Testing

U20 tablets were stored for up to 5 years at either 25° C./60% relative humidity or 30° C./75% relative humidity and their dissolution profiles were tested at various points (3, 6, 9, 12, 18, 24, 36, 48 and 60 months) in an in vitro dissolution test in simulated gastric fluid, in accordance with USP <711>.

Figure 3A:
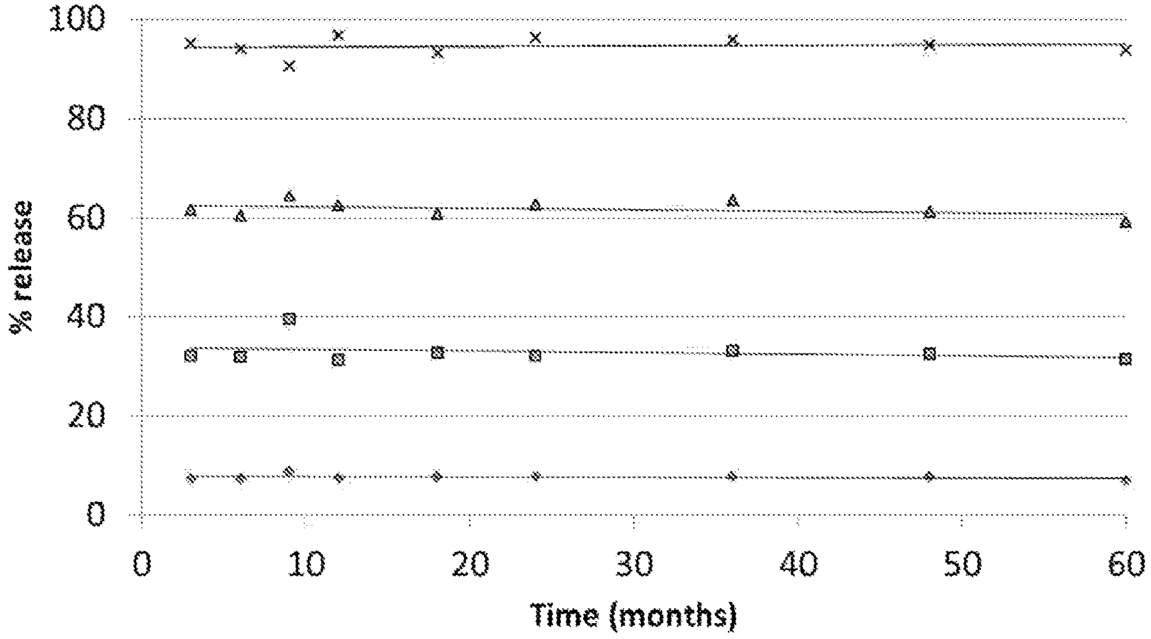
FIGS. 3A and 3B show the % of bexagliflozin released (ordinate) after 1 hour (♦), 3 hours (■), 5 hours (▲), or 8 hours (X) in an in vitro dissolution test. The tablets had been stored for up to 60 months (abscissa) at 25° C.
Figure 3B:
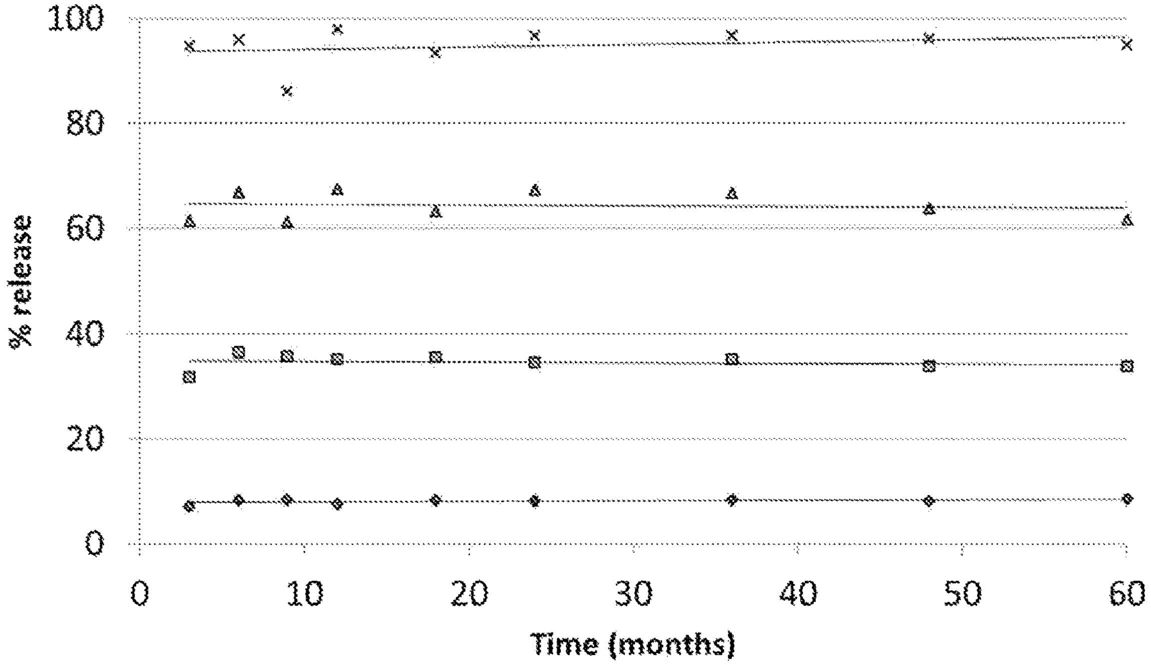

FIGS. 3A and 3B show the mean % of bexagliflozin release from six representative stored tablets per test after 1, 3 5, and 8 hours in simulated gastric fluid. Under both storage conditions, and over the full 5 year period, the % released in the dissolution test after 1 hour stays well below 17%, after 3 hours stays well within the range 20-45% (even between 23-43%), after 5 hours stays well within the range of 45-75% (even between 48-68%), and after 8 hours stays well above 80%.

For samples stored at 25° C., linear regression shows a very slight positive slope for the mean % released after 1 and 8 hours, and a very slight negative slope for the mean % released after 3 and 5 hours. For samples stored at 30° C., linear regression shows a very slight positive slope for the mean % released after 8 hours, and a very slight negative slope for the mean % released after 1, 3 and 5 hours. Under both storage conditions, however, the upper and lower 95% confidence bounds for all four dissolution time-points are greater than and less than zero, respectively, indicating that the slope is not significantly different from zero. Moreover the small magnitude of the changes with time are consistent with the interpretation that the release profile of tablets does not meaningfully vary with storage for up to 5 years.

Example 13—Effectiveness of the U20 Formulation in Randomized Controlled Trials To support late stage clinical development, seven batches of U20 tablets were prepared, including five batches of ≈800,000 tablets. Trials were performed as follows, with between 200-1700 subjects each:

| Design | Comparator | Duration (wks) |
|---|---|---|
| bexagliflozin monotherapy vs. placebo | Placebo | 24 |
| bexagliflozin vs. placebo in subjects with renal impairment | Placebo | 24 |
| bexagliflozin vs. sitagliptin added to metformin | Sitagliptin | 24 |
| bexagliflozin vs. placebo added to metformin | Placebo | 24 |
| bexagliflozin vs. glimepiride added to metformin | Glimepiride | 96 |
| bexagliflozin vs. placebo in subjects with diabetes and increased cardiovascular risks | Placebo | ≈66 to 197 |
| bexagliflozin vs. placebo in subjects with hypertension | Placebo | 36 |

Example 14—Clinical Pharmacology and Food Effect Studies with U20

Additional characterization of the U20 formulation by in vivo experimentation was provided in the course of five clinical pharmacology studies investigating the effects of prior food consumption on the pharmacokinetics of bexagliflozin delivered by the formulation, and of the effects of co-administration of other medications on the pharmacokinetics. Only results from those arms of the latter studies in which an additional medication was not co-administered (i.e., the control arms) are provided in the compilation below.

The U20 tablets were provided following an overnight fast of at least 10 h, with no food or nutrients provided for 4 h following dosing. Tablets were ingested with 240 mL of water but no water was otherwise provided for the hour preceding or the hour following ingestion. No additional medications were permitted to be co-administered.

Geometric mean values for the indicated numbers of subjects (n) were as follows:

| Study | Mass (n) (kg) | $C_{max}$ (n) ng $mL^{-1}$ | $AUC_{0-t}$ (n) ng h $mL^{-1}$ | $AUC_{0-\infty}$ (n) ng h $mL^{-1}$ | $t_{1/2}$ (n) h |
|---|---|---|---|---|---|
| A | 77.1 (18) | 125 (18) | 1101 (18) | 1154 (18) | 10.3 (18) |
| B | 77.3 (18) | 117 (18) | 958 (18) | 1012 (17*) | 12.6 (17*) |
| C | 72.4 (16) | 98 (16) | 698 (16) | 761 (16) | 12.2 (16) |
| D | 77.1 (20) | 96 (20) | 703 (20) | 776 (17*) | 12.4 (17*) |
| E | 72.6 (24) | 134 (24) | 1074 (24) | 1149 (24) | 11.7 (24) |
| Total | 75.2 (96) | 114 (96) | 900 (96) | 972 (92) | 11.8 (92) |

*a terminal elimination phase could not be accurately estimated for some subjects These data show the generally expected variation in pharmacokinetic parameters that result from in vivo analysis of a formulation in cohorts of experimental subjects. The data also illustrate the importance of performing testing in a crossover design, so that each individual serves as his/her own control. The mean value for the dose-normalized $C_{max}$ was 5.7 ng $mL^{-1}$ $mg^{-1}$ bexagliflozin, whereas the corresponding values for the dose-normalized $C_{max}$ for immediate release capsules administered in the fasted state were 12.6, 11.3 and 11.5 ng $mL^{-1}$ $mg^{-1}$ bexagliflozin for capsules containing 6.7, 16.7 and 34 mg bexagliflozin, respectively. The dose-normalized $C_{max}$ for a 50 mg oral solution dosage administered in the fasted state was 13.8 ng $mL^{-1}$ $mg^{-1}$ bexagliflozin. The $AUC_{0-t}$ for a 50 mg oral solution, 2523 ng h $mL^{-1}$, is equivalent to 1009 ng h $mL^{-1}$ for a 20 mg dosage strength. Thus the U20 formulation provides a substantially lower dose-normalized $C_{max}$ while decreasing the dose-normalized $AUC_{0-t}$ only slightly compared to a rapidly absorbed oral solution.

The effects of prior consumption of food have been largely consistent across multiple studies. In a dedicated food effect study with a random sequence subject assignment, the geometric mean $C_{max}$ following ingestion in the fed state was 175.7 ng $mL^{-1}$, compared to 133.7 ng $mL^{-1}$ in the fasted state, or 131.4% of the fasted geometric mean $C_{max}$. The $AUC_{0-t}$ and $AUC_{0-\infty}$ were also increased in the fed state, but by a smaller proportion, 13.9% and 11.1%, respectively. The median $T_{max}$ was 3.5 h following dosing in the fasted state and 5 h following dosing in the fed state. In other studies in which a comparison of pharmacokinetics was made following dosing in different prandial states the median $T_{max}$ in the fasted state was typically 3 h and the median $T_{max}$ in the fed state was typically 5 h. Thus it is a benefit of the formulation of the present invention that the effects of prior consumption of a high fat, high calorie meal are relatively modest and that the pharmacokinetic parameters measured after dosing in either prandial state are not highly variable.

In some clinical pharmacology studies subjects were dosed in the fed state, according to a protocol whereby the subjects fasted for a minimum of 10 hours, then consumed a high calorie, high fat meal within 30 minutes. They ingested U20 tablets 30 minutes after the start of the meal, after which they did not consume additional food for at least 4 h. The results from several studies of this type are shown in the following table, presented as geometric mean values.

| Study | Mass (n) kg | $C_{max}$ (n) ng $mL^{-1}$ | $AUC_{0-t}$ (n) ng h $mL^{-1}$ | $AUC_{0-\infty}$ (n) ng h $mL^{-1}$ | $t_{1/2}$ (n) h |
|---|---|---|---|---|---|
| F | 76.1 (18) | 159 (17) | 1142 (18) | 1205 (17*) | 8.0 (17*) |
| G | 79.9 (16) | 162 (15) | 1056 (16) | 1047 (15*) | 12.2 (15*) |
| H | 77.1 (16) | 159 (16) | 969 (16) | 1035 (16) | 10.5 (16) |
| I | 71.7 (25) | 176 (23) | 1223 (23) | 1276 (23*) | 10.9 (23*) |
| Total | 75.6 (75) | 165 (71) | 1106 (71) | 1165 (71) | 10.1 (71) |

*a terminal elimination phase could not be accurately estimated for some subjects In a drug-drug interaction clinical pharmacology study the effects of the GLP-1 receptor agonist exenatide on the pharmacokinetics of bexagliflozin were studied in a randomized crossover study. It is known that GLP-1 receptor agonists retard gastric emptying and because the bexagliflozin dosage form has a gastroretentive mechanism, the possibility that the retardation would adversely affect bexagliflozin delivery was considered important to address (see e.g., *Guideline on the pharmacokinetic and clinical evaluation of modified release dosage forms* (*EMA/CPMP/EWP/*280/96 *Corr*1) section 5.1.4.2.). In the study, participants were assigned to either receive bexagliflozin alone first, or combined treatment with bexagliflozin and exenatide first. Each group received both treatments alternately, in a crossover fashion (two-period, two-treatment crossover design), with the two treatment periods separated by a 7-day washout period. Systemic exposure, as measured by $AUC_{0-t}$, $AUC_{0-\infty}$, and $C_{max}$ of bexagliflozin following administration 30 min after 10 g of exenatide were delivered by subcutaneous injection, was increased by approximately 48%, 38%, and 25%, respectively compared to bexagliflozin administration alone. The ratio [with 90% confidence interval] of geometric least square means for $AUC_{0-t}$, $AUC_{0-\infty}$, and $C_{max}$ of bexagliflozin with exenatide to those of bexagliflozin alone were 147.50% [130.23%, 167.07%], 137.56% [122.28%, 154.75%], and 125.27% [104.45%, 150.24%], respectively. Although the endpoints of the confidence intervals fell outside of the range 80-125%, indicating an interaction leading to a change in exposure when bexagliflozin was administered following exenatide, the effect of exenatide on bexagliflozin pharmacokinetics was not so large as to jeopardize patient safety or to provoke a recommendation for a change in prescribing pattern. Intra-subject variability for the comparison of bexagliflozin with exenatide to bexagliflozin alone was <22% for the primary PK parameters $AUC_{0-t}$ and $AUC_{0-\infty}$, and approximately 32% for $C_{max}$. Absorption was delayed when bexagliflozin was administered 30 minutes after exenatide injection, with a median $T_{max}$ of 5.00 hours post-dose compared to 2.00 hours post-dose following administration of bexagliflozin alone.

Example 15—Population Pharmacokinetic Modeling

Sparse sampling of the plasma drug concentrations obtained from large diverse populations, combined with pharmacokinetic modeling (population PK modeling), is a tool for exploring potential influences (covariates) on the pharmacokinetics of a drug. Samples for bexagliflozin population PK analysis were obtained from healthy volunteers or diabetic subjects enrolled in studies evaluating pharmacokinetics, from diabetic subjects participating in a sparse sampling program to obtain specimens from multicenter, international clinical trials, from subjects with moderate hepatic impairment and from hypertensive subjects participating in an open label run-in phase (a phase during which all subjects received bexagliflozin). Participants were recruited from North America, Europe and East Asia. The database for analysis contained 884 subjects with 6247 concentration records. The analysis included participants exposed to the T3, T10, T30 and T90 formulations as well as the U5, U10 and U20 formulations. Most of the subjects were exposed to the U20 formulation. Subjects who consented to participate in the sparse sampling program contributed 3 blood samples drawn at variable numbers of hours after dosing, typically six to eight weeks after dosing had begun. Study data included dosing histories (dosage strength, dates and times of dosing), plasma concentrations with corresponding sample collection dates and times, demographic descriptors, laboratory values and concomitant medication records. The model initially contained terms for prandial state, age, weight, body mass index (BMI), body surface area, albumin, alanine transaminase, aspartate transaminase, bilirubin, creatinine clearance, dose, sex, race, disease status, nation and concomitant medications.

The data were well fit by a transit compartment model for the absorption phase coupled with a typical central and peripheral two compartment model for the elimination phase. The inter-individual variations in the absorption rate constant, clearance and central compartment volume were taken to be log-normally distributed, although the actual distributions had fatter tails. Overall, the final PPK model described the observed data very well. Body mass, creatinine clearance, prandial state and Asian race were significant in the PPK model. Heavier patients were found to have lower exposure, whereas reduced creatinine clearance was associated with higher exposure. The fed state was found to lower the $C_{max}$, but AUC and $C_{min}$ were similar to those observed after ingestion in the fasted state. The population PK estimate of the food effect was opposite to that of the definitive food effect study, and by-study analysis of data from the population PK study indicated that the food effect study data appeared to deviate from that of the population as a whole. Asian race was associated with higher $C_{max}$ and clearance.

The population PK simulations for the reference population, consisting of healthy Caucasians, produced a median $C_{max}$ of 112 ng $mL^{-1}$ and a median $C_{min}$ of 14 ng $mL^{-1}$, for a $C_{max}$ to $C_{min}$ ratio of 7.67 and a median 24 h AUC at steady state of 1023 ng h $mL^{-1}$. Simulation values for a diabetic Caucasian population produced median values approximately 10% lower with a $C_{max}$ to $C_{min}$ ratio of 7.66. The first and third quartiles for $C_{min}$ for the latter population were 10.6 and 20.2 ng $mL^{-1}$, above the target concentration of 10 ng $mL^{-1}$ (approximately 10× the in vitro $IC_{50}$). A $C_{min}$ ≥10 ng $mL^{-1}$ and a $C_{max}$ to $C_{min}$ ratio of less than 10 were design objectives for the prolonged release formulation development program.

Example 16—Clinically Acceptable Solid Dosage Forms

The inventors have provided tablet compositions and methods of manufacture that ensure that the extended release formulations of the invention consistently behave according to rigorous and well-accepted standards for in vitro dissolution testing. Not all aspects of a formulation's in vivo behavior can be captured by in vitro testing, however. If a different formulation is designed to impart similar characteristics to the formulation through a materially different composition, or by a different principle or principles for achieving extended release, the in vivo properties can be confirmed to be similar by formal bioequivalence testing. Such testing ensures that the rate and extent of absorption are not significantly or objectionably altered by the new composition.

Gastroretentive tablets of the U5, U10 and U20 formulations have been tested and found to produce statistically significant treatment effects in large scale randomized controlled trials in human diabetes patients. To ensure that further formulations provide similar therapeutic benefits, to be clinically acceptable each batch of tablets destined for human consumption should pass formal dissolution acceptance testing by the three-level process described above (i.e., as documented in USP <711> Acceptance Table 2) with not more than 17% bexagliflozin release by 1 h, between 23% and 43% bexagliflozin release by 3 h, between 45% and 75% bexagliflozin release by 5 h, and not less than 80% bexagliflozin release by 8 h in a test method based on USP Apparatus 1 initially charged with 900 mL of 0.1 N HCl and maintained at 37±0.5° C. with a stirring rate of 50 rpm.

If any substantial change in the formulation is made, in addition to passing these formal dissolution acceptance testing criteria, the tablets must be shown to exhibit in vivo bioequivalence with a reference batch of clinically acceptable tablets for at least the $C_{max}$ and $AUC_{0-t}$ parameters.

A formulation is clinically acceptable if it either (i) has been shown to be clinically effective for the treatment of a disease or condition and is produced in a well-controlled and pre-specified manner by adhering to acceptable ranges for ingredients and processes of manufacture and that passes formal dissolution acceptance testing or (ii) deviates from the original manufacturing ranges for ingredients and/or process of manufacture but that passes formal dissolution acceptance testing and, in addition, is shown to be bioequivalent with the original formulation. The invention encompasses all such clinically acceptable oral solid dosage forms.

The following criteria (from FDA's March 2014 *Guidance for Industry: CMC Post approval Manufacturing Changes To Be Documented in Annual Reports*, Appendix B) illustrate the degree of modification to the formulations which, under ordinary circumstances, would not require a documentation of bioequivalence. In addition, certain other changes may be acceptable as provided in Appendix A of the Guidance.

1. Any change made to comply with the official compendium for the U20 formulation, once specified, except relaxation of an acceptance criterion or deletion of a test.
2. Complete or partial deletion of an ingredient intended to affect only the color, flavor, or fragrance of the formulation without change in other approved specification.
3. Change in nonrelease controlling excipients, expressed as percentage (w/w) of total formulation approved in the original application, less than or equal to the following percent ranges: Filler (lactose monohydrate, MCC)±5%, Lubricant (magnesium stearate)±0.25%, Glidant (colloidal silicon dioxide)±0.1%, and Film Coat (Opadry II blue)±1%.
4. Change in the supplier of an excipient, if the technical grade and specification for the excipient remain the same.
5. Changes in release-controlling excipients (polyethylene oxide, poloxamer 188, glyceryl dibehenate) less than or equal to 5% expressed as a percentage (w/w) of total release-controlling excipients in U20. After the change, the total weight of the dosage form and its specification should remain the same as U20.

It will be understood that the invention is described above by way of example only and modifications may be made while remaining within the scope and spirit of the invention.

The invention claimed is:

1. A tablet comprising:

(a) 1-13% by weight of bexagliflozin;

(b) 30-35% by weight of glyceryl dibehenate;

(c) 16-20% by weight of polyethylene oxide having an average molecular weight of 900,000 g/mol;

(d) 11-13% by weight of lactose;

(e) 10-12% by weight of poloxamer 188;

(f) 18-20% by weight of microcrystalline cellulose;

(g) 1.0-1.5% by weight of colloidal silicon dioxide; and (h) 1.5-2.5% by weight of magnesium stearate, wherein the tablet provides a maximum bexagliflozin plasma concentration in a fasted human subject between 80-150 ng/mL.

2. A tablet comprising:

(a) from 3 mg to 60 mg of bexagliflozin;

(b) from 50 mg to 75 mg of polyethylene oxide having an average molecular weight of 900,000 g/mol;

(c) from 100 mg to 140 mg of glyceryl dibehenate;

(d) from 40 mg to 50 mg of lactose;

(e) from 40 mg to 45 mg of poloxamer 188;

(f) from 60 mg to 80 mg of microcrystalline cellulose;

(g) from 4 mg to 5 mg of colloidal silicon dioxide; and (h) from 6 mg to 9 mg of magnesium stearate, wherein the tablet provides a maximum bexagliflozin plasma concentration in a fasted human subject between 80-150 ng/mL.

3. The tablet of claim 2, comprising (a) 20 mg of bexagliflozin;

(b) 65 mg of polyethylene oxide having an average molecular weight of 900,000 g/mol;

(c) 120 mg of glyceryl dibehenate powder;

(d) 45 mg of spray-dried lactose monohydrate;

(e) 42 mg of micronized poloxamer 188;

(f) 70 mg of microcrystalline cellulose;

(g) 4.5 mg of amorphous anhydrous colloidal silicon dioxide; and (h) 7.5 mg of magnesium stearate.

4. The tablet of claim 2 further comprising from 10 mg to 12 mg of a film coating comprising polyvinyl alcohol, titanium dioxide, and polyethylene glycol 3350.

5. The tablet of claim 3 further comprising a film coating consisting of 11.22 mg of a mixture of polyvinyl alcohol, titanium dioxide, polyethylene glycol 3350, talc, disodium 2-[[4-[ethyl-[(3-sulfonatophenyl)methyl]amino]phenyl]-[4-[ethyl-[3-sulfonatophenyl)methyl]azaniumylidene]cyclohexa-2,5-dien-1-ylidene]methyl]benzenesulfonate, and indigo carmine.

6. The tablet of claim 2, wherein the tablet releases 20-45% by weight of bexagliflozin after 3 hours, according to an in vitro dissolution test performed with a United States Pharmacopoeia Apparatus 1 at 50 rpm with 900 mL of 0.1 N HCl at 37±0.5° C.

7. The tablet of claim 2, wherein the tablet releases 45-75% by weight of bexagliflozin after 5 hours, according to an in vitro dissolution test performed with a United States Pharmacopoeia Apparatus 1 at 50 rpm with 900 mL of 0.1 N HCl at 37±0.5° C.

* * * * *